United States Patent [19]

Hanagan

[11] Patent Number: 4,789,393
[45] Date of Patent: Dec. 6, 1988

[54] HERBICIDAL PYRIDINE SULFONAMIDES

[75] Inventor: Mary A. Hanagan, Newark, Del.

[73] Assignee: E. I. Du Pont de Nemours and Company, Wilmington, Del.

[21] Appl. No.: 936,105

[22] Filed: Nov. 28, 1986

Related U.S. Application Data

[63] Continuation-in-part of Ser. No. 837,392, Mar. 7, 1986, abandoned.

[51] Int. Cl.⁴ .................... C07D 401/12; A01N 43/54
[52] U.S. Cl. .......................................... 71/92; 544/320
[58] Field of Search ...................... 71/92; 544/320, 331

[56] References Cited

U.S. PATENT DOCUMENTS 4,435,206  3/1984  Levitt ........................................ 71/92
4,518,776  5/1985  Meyer et al. ........................... 544/206
4,521,597  6/1985  Kristinsson et al. ..................... 544/3
4,522,645  6/1985  Levitt ........................................ 71/93
4,544,401 10/1985  Levitt ........................................ 71/92
4,549,898 10/1985  Böhner et al. ........................... 71/90
4,609,397  9/1986  Wexler ...................................... 71/92
4,690,705  9/1987  Christensen ............................. 71/90

FOREIGN PATENT DOCUMENTS 870436  1/1987  South Africa.

*Primary Examiner*—John M. Ford

[57] ABSTRACT

N,N-dimethyl-2-(aminosulfonyl)-3-pyridine carboxamides are useful as agricultural chemicals. In particular, the compounds are useful as herbicides which show significant herbicidal activity on grasses and yet have the unexpected property of being safe to corn.

36 Claims, No Drawings

HERBICIDAL PYRIDINE SULFONAMIDES

RELATED APPLICATION

This application is a continuation-in-part of my copending application U.S. Ser. No. 837,392, filed Mar. 7, 1986, now abandoned.

BACKGROUND OF THE INVENTION

This invention relates to novel N,N-dimethyl-2-(aminosulfonyl)-3-pyridine-carboxamides. The compounds of this invention and their agriculturally suitable salts are useful as agricultural chemicals, and in particular, as herbicides which may be selective to corn.

U.S. Pat. No. 4,544,401 and U.S. Pat. No. 4,435,206 disclose herbicidal pyridinesulfonylureas.

U.S. Pat. No. 4,518,776 (Swiss priority 7/19/82) and EP-A-101,670 (Swiss priority 8/23/82, published 2/29/84) disclose, in part, a process for the preparation of compounds of formula

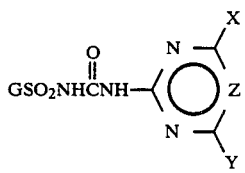

wherein

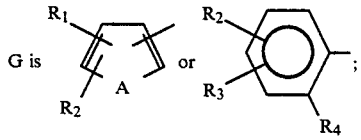

$R_1$ is, among other values, $C(O)NHC_1$-$C_4$ alkyl or $C(O)N(C_1$-$C_4$ alkyl$)_2$;

$R_2$ is H, halogen, $CF_3$, $NO_2$, $C_1$-$C_4$ alkyl or $C_1$-$C_4$ alkoxy;

A is O, S, $NR_5$ or —C=N—;

X is $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ alkylamino or di-$C_1$-$C_4$ alkylamino;

Y is $C_1$-$C_4$ alkyl, $C_1$-$C_4$ alkoxy or $C_1$-$C_4$ haloalkoxy; and

Z is CH or N.

U.S. Pat. No. 4,518,776 generically discloses but does not claim compounds of the invention. (No pyridine carboxamides are specifically disclosed.)

EP-A-107,624 (Swiss priority 10/25/82, published 5/2/84) discloses, in part, a process for the preparation of compounds of formula

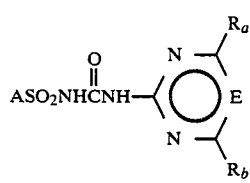

wherein

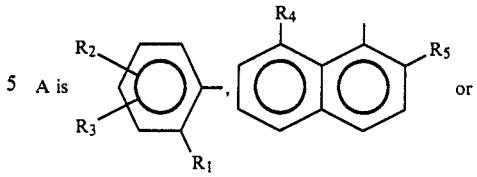

$R_3$ is H, halogen, $NO_2$, $OCH_3$ or $CF_3$;

$R_5$ is, among others, $CONR_8R_9$;

$R_8$ is H, $C_1$-$C_5$ alkyl, $C_1$-$C_5$ cyanoalkyl, $OCH_3$, $OC_2H_5$ or $C_3$-$C_5$ alkenyl;

$R_9$ is H, $C_1$-$C_5$ alkyl or $C_3$-$C_5$ alkenyl;

Y is O, S or $C(R_6)$=N; $R_a$ is H, halogen, $C_1$-$C_5$ alkyl, $C_1$-$C_5$ haloalkyl, $C_1$-$C_5$ alkoxy, $C_1$-$C_5$ haloalkoxy, $C_1$-$C_5$ alkylthio, $C_2$-$C_{10}$ alkoxyalkyl or $C_2$-$C_{10}$ alkoxyalkoxy;

$R_b$ is the same as $R_a$ or $NR_cR_d$; and

E is CH or N. This application generically discloses but does not claim compounds of the invention. (No pyridine carboxamides are specifically disclosed.)

U.S. Pat. No. 4,549,898 discloses herbicidal sulfonylureas of formula

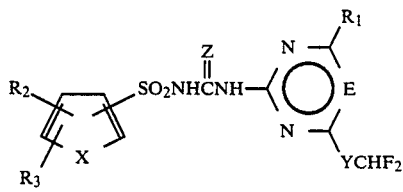

wherein

X is O, S, $NR_4$ or $C(R_5)$=N;

Y is O or S;

Z is O or S;

E is N or CH;

$R_1$ is H, $C_1$-$C_4$ alkyl, $C_1$-$C_4$ haloalkyl, $C_1$-$C_4$ haloalkoxy, $C_1$-$C_4$ alkoxy, halogen, $C_1$-$C_4$ alkylthio, $NR_6R_7$ or alkoxyalkyl containing not more than 4 carbon atoms;

$R_2$ is, among others, $CONR_6R_7$;

$R_3$ is H, halogen, $C_1$-$C_3$ alkyl, $OCH_3$ or $CF_3$;

$R_5$ is H, $NO_2$, F, Cl, Br, $CH_3$, $CF_3$, $S(O)_nC_1$-$C_3$ alkyl, $COC_1$-$C_4$ alkoxy or $C_1$-$C_3$ alkoxy;

$R_6$ is H, $C_1$-$C_6$ alkyl, $C_1$-$C_4$ cyanoalkyl, methoxy or ethoxy; and $R_7$ is H, $C_1$-$C_6$ alkyl or $C_3$-$C_6$ alkenyl. Although compounds of the invention are generically disclosed, no examples of pyridineamides are listed in the tables.

EP-A-155,767, published 9/25/85, discloses, in part, herbicidal sulfonylureas of formula

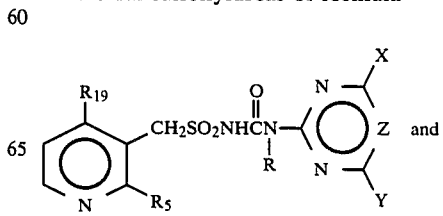

and

-continued

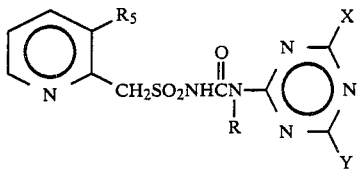

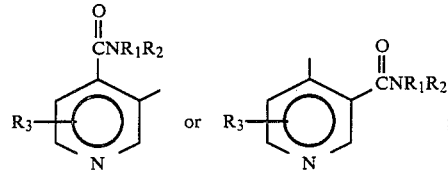

wherein

R is H or CH$_3$;

R$_5$ is H, CH$_3$, Cl, Br, CO$_2$R$_{15}$, C(O)NR$_{16}$R$_{17}$, SO$_2$NR$_{16}$R$_{17}$, SO$_2$N(OCH$_3$)CH$_3$, SO$_2$R$_{18}$ or NO$_2$;

R$_{16}$ is C$_1$-C$_2$ alkyl;

R$_{17}$ is C$_1$-C$_2$ alkyl;

R$_{19}$ is CH$_3$, Cl, Br, NO$_2$, C$_1$-C$_2$ alkylthio or C$_1$-C$_2$ alkylsulfonyl;

X is CH$_3$, OCH$_3$, Cl, Br, OCH$_2$CF$_3$ or OCHF$_2$;

Y is C$_1$-C$_3$ alkyl, CH$_2$F, cyclopropyl, C≡CH, OCH$_3$, OC$_2$H$_5$, CH$_2$OCH$_3$, NH$_2$, NHCH$_3$, N(CH$_3$)$_2$, OCH$_2$CH$_2$F, CF$_3$, SCH$_3$, OCH$_2$CH═CH$_2$, OCH$_2$C≡CH, OCH$_2$CH$_2$OCH$_3$, CF(OCH$_3$)$_2$,

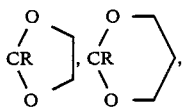

CR(OCH$_2$CH$_3$)$_2$ or OCF$_2$H; and

Z is CH or N.

There is still a need for improved agricultural chemicals, especially herbicides which may be selective for corn. According to this invention, such herbicides have been found.

SUMMARY OF THE INVENTION

This application pertains to novel compounds of Formula I, agriculturally suitable compositions containing them, and their method-of-use as preemergent and/or postemergent herbicides or plant growth regulants.

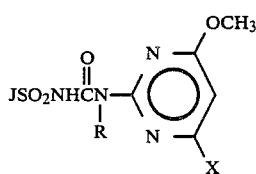

wherein

J is

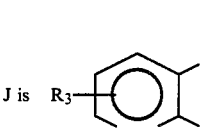 , 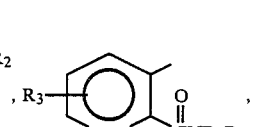 , 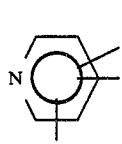

J-1          J-2

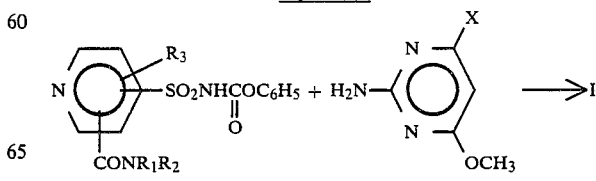

J-3          J-4

R is H or CH$_3$;

R$_1$ is H or C$_1$-C$_3$ alkyl;

R$_2$ is C$_1$-C$_3$ alkyl or C$_1$-C$_2$ alkoxy; or

R$_1$ and R$_2$ may be taken together to form —(CH$_2$)$_n$—, wherein n is 2, 3 or 4;

R$_3$ is H, Cl, F, Br, CH$_3$, CF$_3$, OCH$_3$ or OCF$_2$H; and

X is CH$_3$, CH$_2$F, CH$_2$CH$_3$, OCH$_3$, OCH$_2$CH$_3$, Cl, OCF$_2$H or CH$_2$OCH$_3$.

Preferred for reasons of their greater herbicidal activity and/or more favorable ease of synthesis are:

(1) Compounds of Formula I where R is H.
(2) Compounds of Preferred 1 where J is J-1.
(3) Compounds of Preferred 1 where J is J-2.
(4) Compounds of Preferred 1 where J is J-3.
(5) Compounds of Preferred 1 where J is J-4.
(6) Compounds of Preferred 2 where X is OCH$_3$, CH$_3$ or Cl.
(7) Compounds of Preferred 6 where R$_3$ is H, F or Cl.
(8) Compounds of Preferred 7 where R$_2$ is CH$_3$, CH$_2$CH$_3$ or OCH$_3$; and R$_3$ is H.
(9) Compounds of Preferred 3 where X is OCH$_3$, CH$_3$ or Cl.
(10) Compounds of Preferred 9 where R$_3$ is H, F or Cl.
(11) Compounds of Preferred 10 where R$_2$ is CH$_3$, CH$_2$CH$_3$ or OCH$_3$; and R$_3$ is H.
(12) Compounds of Preferred 4 where X is OCH$_3$, CH$_3$ or Cl.
(13) Compounds of Preferred 12 where R$_3$ is H, F or Cl.
(14) Compoudns of Preferred 13 where R$_2$ is CH$_3$, CH$_2$CH$_3$ or OCH$_3$; and R$_3$ is H.
(15) Compounds of Preferred 5 where X is OCH$_3$, CH$_3$ or Cl.
(16) Compounds of Preferred 15 where R$_3$ is H, F or Cl.
(17) Compounds of Preferred 16 where R$_2$ is CH$_3$, CH$_2$CH$_3$ or OCH$_3$; and R$_3$ is H.

Specifically preferred for its greatest herbicidal activity with concurrent safety to corn and more favorable ease of synthesis is:

2-[[(4,6-dimethoxypyrimidin-2-yl)aminocarbonyl]aminosulfonyl]-N,N-dimethyl-3-pyridinecarboxamide, m.p. 142°–159° C. (dec).

DETAILS OF THE INVENTION

Compounds of Formula I can be prepared by the methods described in Equations 1 and 2.

Equation 1

The reaction shown in Equation 1 is carried out by contacting the phenyl carbamate of Formula (3) with the aminoheterocycle of Formula (2) in an inert organic solvent such as dioxane or tetrahydrofuran at temperatures of about 20° to 100° C. for a period of about one-half to twenty-four hours. The product can be isolated by evaporation of the reaction solvent and purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

The phenyl carbamates of Formula (3) can be prepared by the reaction of a sulfonamide of Formula (4), Equation 2, with diphenylcarbonate in the presence of a base as described in EPO No. 44,808 or South African patent application No. 825042 (or modifications thereof).

Equation 2

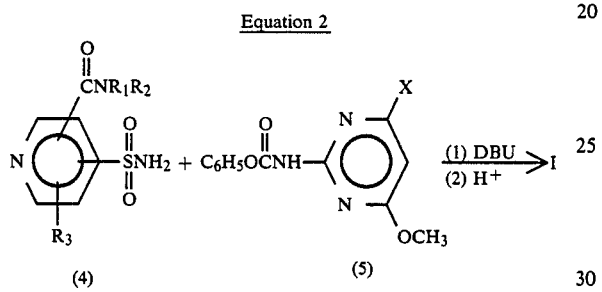

(4)  (5)

The reaction of Equation 2 can be carried out by contacting equimolar amounts of the sulfonamide of Formula (4) with a heterocyclic phenyl carbamate of Formula (5) in the presence of an equimolar amount of 1,8-diazabicyclo[5.4.0]undec-7-ene (DBU), by methods analogous to those described in South African patent application No. 830441. The phenyl carbamates of Formula (5) can be prepared by methods (or modifications thereof) described in South African patent application No. 825671 and South African patent application No. 825045. (Please summarize briefly.)

The sulfonamides of Formula (4) can be prepared by the methods shown in Equations 3, 4 and 5.

Halopyridine-carboxylic acid derivatives of Formula (6) (Equation 3) can be prepared by methods known in the art or modifications thereof such as those described by S. G. Woods et al., *J. Heterocyclic Chem.*, Vol. 21, p. 97 (1984) by L. Testaferri et al., in *Tetrahedron*, Vol. 41, P. 1373 (1975) and in *The Chemistry of Heterocyclic Compounds: Pyridine and Its Derivatives*, Vol. 14, Interscience Publishers, Inc., New York.

Compound (6) is treated with potassium benzylthiolate in N,N-dimethylformamide (DMF) at temperatures of about 100° to 150° C. for a period of about two hours as described by S. G. Woods et al. (op. cit.). The product (7) can be isolated by acidification and filtration.

The acid (7) is converted to amide (9) by treatment with excess thionylchloride and amination with two moles of dialkylamine in an inert organic solvent such as tetrahydrofuran. The product (9) can be isolated by evaporation of the reaction solvent.

The reaction shown in Equation 3(d) is carried out by contacting sulfide (9) with sodium hypochlorite in an aqueous solution of hydrochloric acid using procedures which are known in the art such as those disclosed in South African patent application No. 84/8844. The sulfonyl chloride is converted to sulfonamide (4) by contact with ammonia. The product can be isolated by evaporation of the solvent.

Equation 3

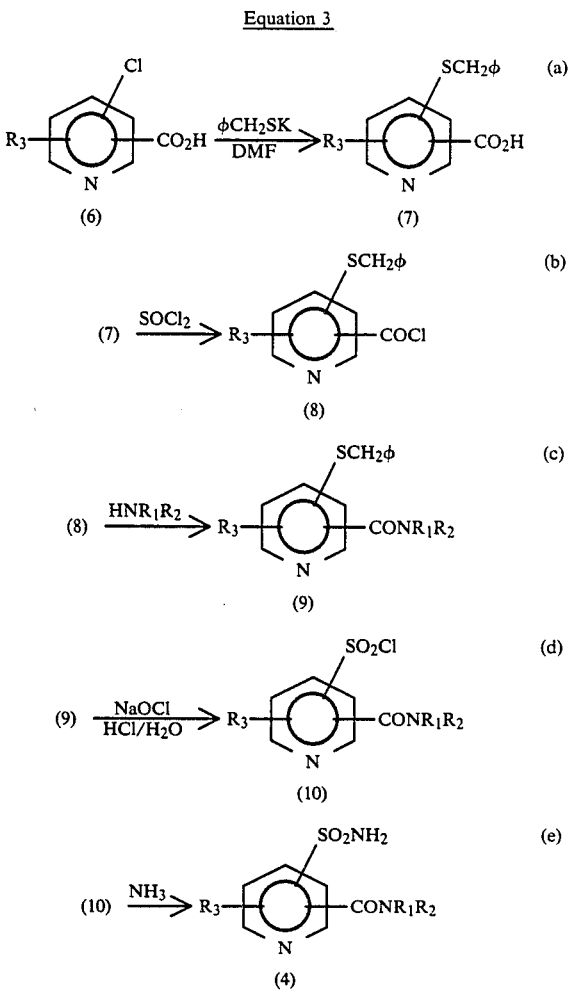

Equation 4

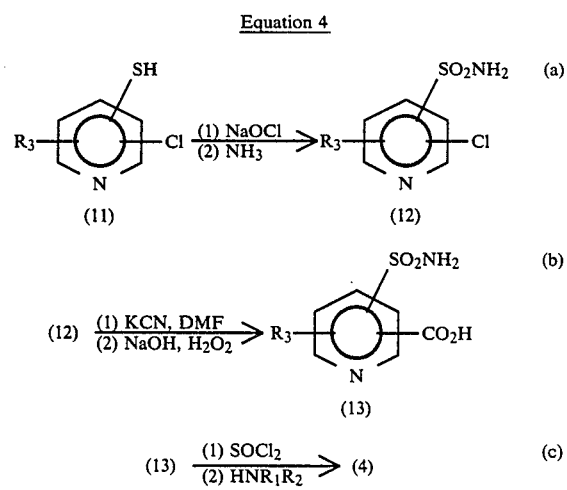

Halopyridinethiol derivatives of Formula (11) (Equation 4) can be prepared by methods known in the art or modifications thereof such as those described in U.S. Pat. No. 2,456,258 and by Grassetti et al. in *J. Chromatography*, Vol. III, p. 121 (1969) or from the halopyridin-4-ols as described in Den Hertog et al. in *Rec. Trav.*

*Chim.*, Vol. 70, p. 353 (1951) and M. S. Newman and H. A. Karnes, in *J. Org. Chem.*, Vol. 31, p. 410 (1966). The reaction shown in Equation 4a is carried out by contacting thiol (11) with sodium hypochlorite according to the procedure of L. H. McKendry et al. (op. cit.). Treatment of the sulfonamide (12) with potassium cyanide using methods described by Testaferri et al. (op. cit.) and hydrolysis with sodium hydroxide and hydrogen peroxide (March, *Advanced Organic Chemistry*, 3rd Edition, pp. 809–810, McGraw-Hill, Inc., New York, 1977) gives acid (13). The acid is converted to amide (4) by contact with thionyl chloride and amination with two moles of dialkylamine. The product can be isolated by evaporation of the solvent.

Equation 5

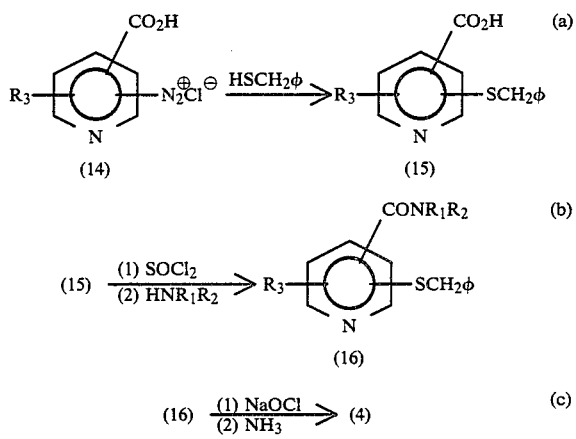

Diazonium derivatives of Formula (14) (Equation 5) can be prepared by methods known in the art or by modifications thereof such as those described by Blanz et al. in *J. Med. Chem.*, Vol. 6, p. 185 (1963). The reaction shown in Equation 5a is carried out by contacting diazonium salt (14) with benzylthiol. Conversion of the acid (15) to amide (16) is accomplished by treatment with thionyl chloride and amination with two moles of dialkylamine. Reaction 5c is carried out according to the procedure of L. H. McKendry et al. (op. cit.) to give sulfonamide (4).

Equation 6

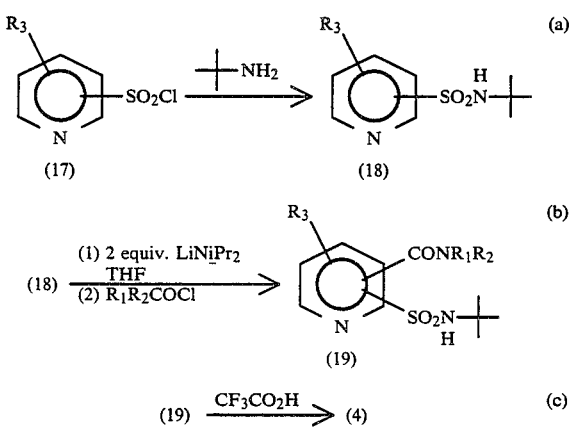

Pyridinesulfonyl halides of Formula (17) (Equation 6) can be prepared from the corresponding thiols, sulfides or sulfonic acids by methods known in the art, including those described above, or modifications thereof. The reaction shown in Equation 6a is carried out by contacting sulfonyl halide (17) with tert-butylamine. The ortho-carboxamide (19) is prepared from (18) by a modification of the method described by Quéguiner in *Synthesis*, p. 822 (1983). The tert-butylsulfonamide (19) is converted to amide (4) by contact with trifluoroacetic acid.

Equation 7

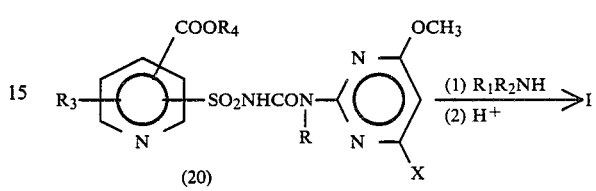

Pyridine ester sulfonylureas of Formula (20) can be prepared as described in U.S. Pat. No. 4,544,401, U.S. Pat. No. 4,435,206 and EP-A-13,480. The reaction shown in Equation 7 is accomplished by contacting ester (20) with the appropriate amine, followed by neutralization.

The heterocyclic amines of Formula (2) are known compounds.

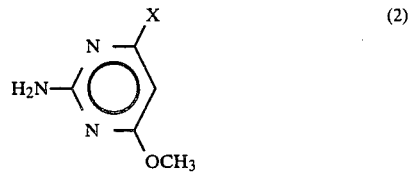

For a review of the synthesis and reactions of 2-aminopyrimidines see *The Chemistry of Heterocyclic Compounds*, Vol. 16, Wiley-Interscience, New York (1962). U.S. Pat. No. 4,540,782 describes methods for the preparation of pyrimidines of Formula (2) wherein X is $OCF_2H$.

Agriculturally suitable salts of compounds of Formula I are also useful herbicides and can be prepared by well-known methods including those described in U.S. Pat. No. 4,127,405.

The following Examples illustrate syntheses of the compounds of this invention. Temperatures are in degrees Celsius.

EXAMPLE 1

N,N-Dimethyl-2-(phenylmethylthio)-3-pyridinecarboxamide

A solution of 25.0 g (223 mmol) of potassium t-butoxide in 100 ml of dimethylformamide was cooled to 0° C. and 22 ml (186 mmol) of benzyl mercaptan added dropwise at 0° C. After addition was complete, the reaction mixture was allowed to warm to 25° C. and stirred at this temperature for 15 minutes. The reaction mixture was then re-cooled to 0° C. and 34.0 g (186 mmol) of N,N-dimethyl-2-(chloro)-3-pyridinecarboxamide added in one portion. After an exotherm to 50° C., the mixture was heated at 80° C. for 1.5 hour. The mixture was cooled, poured into 100 ml of water and extracted with ether. The combined organic extracts were washed twice with water, then brine and dried over sodium sulfate. Concentration gave 19.2 g of a viscous yellow oil. IR (Nujol) 1640 (CONMe$_2$) cm$^{-1}$.

NMR (CDCl$_3$): δ 2.72 (s, 3H, NCH$_3$); 3.04 (s, 3H, NCH$_3$); 4.49 (s, 2H, SCH$_2$C$_6$H$_5$); 6.97–7.17 (m, 1H); 7.18–7.57 (m, 6H); and 8.50 (d of d, 1H).

EXAMPLE 2

N,N-Dimethyl-2-aminosulfonyl-3-pyridinecarboxamide

A mixture of 4.4 ml of concentrated hydrochloric acid, 66 ml of methylene chloride, 34 ml of water and 4.0 g (14.7 mmol) of the N,N-dimethyl-2-(phenylmethylthio)-3-pyridinecarboxamide was cooled to 0° C. Maintaining a temperature of −5° to 3° C., 60 ml (40.5 mmol) of 5% sodium hypochlorite was added dropwise over 15 minutes. The resulting yellow emulsion was stirred at 0° C. an additional 20 minutes. The reaction mixture was then poured into water and extracted with methylene chloride. The combined organic extracts were kept at 0° C. and washed with a saturated sodium bisulfite solution and dried over sodium sulfate. After 30 minutes, the yellow solution was filtered into a reaction flask and cooled to −78° C. and 5 ml (431 mmol) of dry ammonia added. The reaction mixture was allowed to warm to room temperature and the solvent removed under reduced pressure. The resulting solid was slurried with 5 ml of water and the insoluble white solid collected by filtration to provide 2.0 g of the subject compound, m.p. 198°–209° C.(d).

NMR (DMSO): δ 2.70 (s, 3H, NCH$_3$); 2.93 (s, 3H, NCH$_3$); 7.60–7.75 (m, 1H); 7.90 (m, 1H); and 8.75 (m, 1H).

EXAMPLE 3

N,N-Dimethyl-2-[[(4,6-dimethoxypyrimidin-2-yl)aminocarbonyl]aminosulfonyl]-3-pyridinecarboxamide To a suspension of 0.50 g (2.2 mmol) N,N-dimethyl-2-(aminosulfonyl)-3-pyridinecarboxamide and 0.60 g (2.2 mmol) of 4,6-dimethoxypyrimidin-2-yl phenyl carbamate in 3 ml acetonitrile was added 0.32 ml (2.2 mmol) of 1,8-diazabicyclo[5.4.0]undec-7-ene (DBU). The resulting solution was stirred at room temperature for 7 minutes. The addition of 6 ml of water followed by the dropwise addition of 10% hydrochloric acid produced a white precipitate which was collected by filtration to provide 0.75 g of the subject compound, m.p. 142°–159° C.(d). IR (Nujol) 1720 (CO), 1609, 1365, 1162 cm$^{-1}$.

NMR (DMSO): δ 2.80 (s, 3H, NCH$_3$); 2.93 (s, 3H, NCH$_3$); 3.89 (s, 6H, OCH$_3$); 6.02 (s, 1H); 7.70–7.80 (m, 1H); 8.00 (m, 1H); 8.72 (m, 1H); 10.62 (s, 1H, NH); and 12.75 (s, 1H, NH).

EXAMPLE 4

2-(Phenylmethylthio)-3-pyridinecarboxylic acid 200 parts 2-mercaptonicotinic acid, 970 parts of water, 215 parts of 50% NaOH, and 164 parts of benzyl chloride were combined and the resulting solution was refluxed for 2 hours. After dilution with 2580 parts of water, the solution was acidified with 207 parts of 36% HCl. The resulting slurry was cooled and filtered. The wet cake was washed with water and dried to give 307 parts (97.1%) of 2-(phenylmethylthio)-3-pyridinecarboxylic acid, m.p. 190°–193° C.

EXAMPLE 5

N,N-Dimethyl-2-(phenylmethylthio)-3-pyridinecarboxamide

A mixture of 29.7 parts of thionylchloride, 50.0 parts of 2-(phenylmethylthio)-3-pyridinecarboxylic acid, and 225 parts of ethyl acetate was refluxed for 1.6 hours. The resulting solution of 2-(phenylmethylthio)-3-pyridinecarbonyl chloride was cooled to 5° C. While maintaining the temperature at approximately 10° C., 70 parts of 40% dimethylamine in water were added. The pH was adjusted to 4.0 with 36% HCl and the lower aqueous layer was decanted. Water was added to the ethyl acetate layer and the resulting mixture was distilled until the ethyl acetate was removed. After cooling and seeding, N,N-dimethyl-2-(phenylmethylthio)-3-pyridinecarboxamide was recovered by filtration, washed with water, and dried. This gave 52.1 parts (93.9%), melting point 61°–63° C.

EXAMPLE 6

2-(Chlorosulfonyl)-N,N-dimethyl-3-pyridinecarboxamide

A mixture of 60 parts N,N-dimethyl-2-(phenylmethylthio)-3-pyridinecarboxamide, 240 parts of water, and 372 parts of Freon ®TF was kept at 2° C. by external cooling while 59 parts of Cl$_2$ was passed in during 10 minutes. The solids that formed were collected by filtration, washed with ice water (2×100 parts) and Freon ®TF (2×55 parts), and dried by drawing dry air through the filter. This gave 46.7 parts (85.2% yield) of 3-((dimethylamino)carbonyl))-2-pyridinesulfonyl chloride, melting point 110°–114° C. If this material is to be kept for any length of time, it should be stored at <0° C.

EXAMPLE 7

2-(Aminosulfonyl)-N,N-dimethyl-3-pyridinecarboxamide

Anhydrous NH$_3$ (9 parts) was sparged into a mixture of 45.0 parts of sulfonyl chloride and 120 parts of THF. The NH$_3$ addition required 40 minutes during which time the temperature was kept below 10° C. Water (115 parts) was added and the pH was adjusted to 7.5 with 13 parts of 36% HCl. The resulting mixture was then distilled until the pot temperature reached 79° C. After cooling, the product was collected by filtration, washed with cold water, and dried. This gave 32.4 parts (78.2%) of 2-(aminosulfonyl)-N,N-dimethyl-3-pyridinecarboxamide, melting point 188°–191° C.

EXAMPLE 8

Phenyl[3-[(N,N-dimethylaminocarbonyl)-2-pyridinyl]-sulfonyl]carbamate

Phenyl chloroformate (30.4 parts) was added over 25 minutes to a mixture of 20.0 parts of 2-(aminosulfonyl)-N,N-dimethyl-3-pyridinecarboxamide, 30.3 parts of 50% NaOH, and 63 parts of acetone. The temperature was kept between 0° and 5° C. After stirring for another 20 minutes, 157 parts of water was added. The resulting thin slurry was filtered. The filtrate was acidified to pH 2 with 20 parts of 36% HCl. The precipitated solids were recovered by filtration, washed with water, and dried. This gave 26.3 parts (86.3%) of the phenyl ester of [3-[[(dimethylaminocarbonyl)-2-pyridinyl]sulfonyl]-carbamic acid, m.p. 150°–154° C.

EXAMPLE 9

N,N-Dimethyl-2-[[(4,6-dimethoxypyrimidin-2-yl)aminocarbonyl]aminosulfonyl]-3-pyridinecarboxamide 12.0 parts of the carbamate of Example 8, 5.33 parts of 2-amino-4,6-dimethoxypyrimidine, and 36 parts of ethyl acetate were refluxed for 1.0 hour. The slurry was cooled and filtered. The solids were washed with ethyl acetate and dried to give 12.3 parts (87.3% yield) of the subject compound, m.p. 184°–185° C.

The following compounds may be prepared by one skilled in the art using the procedures described earlier and exemplified in Examples 1–9.

TABLE 1

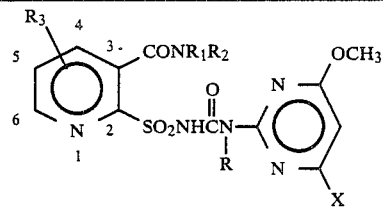

| R | $R_1$ | $R_2$ | $R_3$ | X | m.p. (°C.) |
|---|---|---|---|---|---|
| H | H | $CH_3$ | H | $OCH_3$ | |
| H | H | $CH_2CH_3$ | H | $OCH_3$ | |
| H | H | $CH_2CH_2CH_3$ | H | $OCH_3$ | |
| H | H | $CH(CH_3)_2$ | H | $OCH_3$ | |
| H | H | $OCH_3$ | H | $OCH_3$ | |
| H | H | $OCH_2CH_3$ | H | $OCH_3$ | |
| H | H | $CH_3$ | H | $CH_3$ | |
| H | H | $CH_2CH_3$ | H | $CH_3$ | |
| H | H | $CH_2CH_2CH_3$ | H | $CH_3$ | |
| H | H | $CH(CH_3)_2$ | H | $CH_3$ | |
| H | H | $OCH_3$ | H | $CH_3$ | |
| H | H | $OCH_2CH_3$ | H | $CH_3$ | |
| H | H | $CH_3$ | H | Cl | |
| H | H | $CH_2CH_3$ | H | Cl | |
| H | H | $CH_2CH_2CH_3$ | H | Cl | |
| H | H | $CH(CH_3)_2$ | H | Cl | |
| H | H | $OCH_3$ | H | Cl | |
| H | H | $OCH_2CH_3$ | H | Cl | |
| H | H | $CH_3$ | H | $CH_2F$ | |
| H | H | $CH_2CH_3$ | H | $CH_2F$ | |
| H | H | $OCH_3$ | H | $CH_2F$ | |
| H | H | $CH_3$ | H | $OCF_2H$ | |
| H | H | $CH_2CH_3$ | H | $OCF_2H$ | |
| H | H | $OCH_3$ | H | $OCF_2H$ | |
| H | H | $CH_3$ | H | $OCH_2CH_3$ | |
| H | H | $CH_2CH_3$ | H | $OCH_2CH_3$ | |
| H | H | $OCH_3$ | H | $OCH_2CH_3$ | |
| H | H | $CH_3$ | H | $CH_2OCH_3$ | |
| H | H | $CH_2CH_3$ | H | $CH_2OCH_3$ | |
| H | H | $OCH_3$ | H | $CH_2OCH_3$ | |
| $CH_3$ | H | $CH_3$ | H | $OCH_3$ | |
| $CH_3$ | H | $OCH_3$ | H | $OCH_3$ | |
| $CH_3$ | H | $CH_3$ | H | $CH_3$ | |
| $CH_3$ | H | $OCH_3$ | H | $CH_3$ | |
| $CH_3$ | H | $CH_3$ | H | Cl | |
| $CH_3$ | H | $OCH_3$ | H | Cl | |
| $CH_3$ | H | $CH_3$ | H | $CH_2F$ | |
| $CH_3$ | H | $CH_3$ | H | $OCF_2H$ | |
| $CH_3$ | H | $CH_3$ | H | $CH_2OCH_3$ | |
| H | $CH_3$ | $CH_3$ | H | $OCH_3$ | 142–159 d |
| H | $CH_3$ | $CH_2CH_3$ | H | $OCH_3$ | 123–125 d |
| H | $CH_3$ | $CH_2CH_2CH_3$ | H | $OCH_3$ | |
| H | $CH_3$ | $CH(CH_3)_2$ | H | $OCH_3$ | |
| H | $CH_3$ | $OCH_3$ | H | $OCH_3$ | 174–177 d |
| H | $CH_3$ | $OCH_2CH_3$ | H | $OCH_3$ | |
| H | $CH_3$ | $CH_3$ | H | $CH_3$ | 151–152 d |
| H | $CH_3$ | $CH_2CH_3$ | H | $CH_3$ | 133–134 d |
| H | $CH_3$ | $CH_2CH_2CH_3$ | H | $CH_3$ | |
| H | $CH_3$ | $CH(CH_3)_2$ | H | $CH_3$ | |
| H | $CH_3$ | $OCH_3$ | H | $CH_3$ | 130 d |
| H | $CH_3$ | $OCH_2CH_3$ | H | $CH_3$ | |
| H | $CH_3$ | $CH_3$ | H | Cl | 144–145 d |
| H | $CH_3$ | $CH_2CH_3$ | H | Cl | |
| H | $CH_3$ | $CH_2CH_2CH_3$ | H | Cl | |
| H | $CH_3$ | $CH(CH_3)_2$ | H | Cl | |
| H | $CH_3$ | $OCH_3$ | H | Cl | |
| H | $CH_3$ | $OCH_2CH_3$ | H | Cl | |
| H | $CH_3$ | $CH_3$ | H | $CH_2F$ | |
| H | $CH_3$ | $CH_2CH_3$ | H | $CH_2F$ | |
| H | $CH_3$ | $OCH_3$ | H | $CH_2F$ | |
| H | $CH_3$ | $CH_3$ | H | $OCF_2H$ | |

TABLE 1-continued

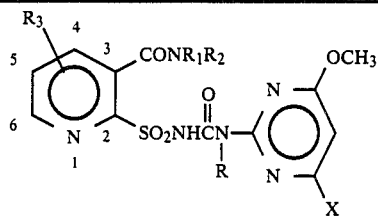

| R | R₁ | R₂ | R₃ | X | m.p. (°C.) |
|---|----|----|----|---|------------|
| H | CH₃ | CH₂CH₃ | H | OCF₂H | |
| H | CH₃ | OCH₃ | H | OCF₂H | |
| H | CH₃ | CH₃ | H | OCH₂CH₃ | |
| H | CH₃ | CH₂CH₃ | H | OCH₂CH₃ | |
| H | CH₃ | OCH₃ | H | OCH₂CH₃ | |
| H | CH₃ | CH₃ | H | CH₂OCH₃ | |
| H | CH₃ | CH₂CH₃ | H | CH₂OCH₃ | |
| H | CH₃ | OCH₃ | H | CH₂OCH₃ | |
| CH₃ | CH₃ | CH₃ | H | OCH₃ | |
| CH₃ | CH₃ | OCH₃ | H | OCH₃ | |
| CH₃ | CH₃ | CH₃ | H | CH₃ | |
| CH₃ | CH₃ | OCH₃ | H | CH₃ | |
| CH₃ | CH₃ | CH₃ | H | Cl | |
| CH₃ | CH₃ | OCH₃ | H | Cl | |
| CH₃ | CH₃ | CH₃ | H | CH₂F | |
| CH₃ | CH₃ | CH₃ | H | OCF₂H | |
| CH₃ | CH₃ | CH₃ | H | CH₂OCH₃ | |
| H | CH₂CH₃ | CH₂CH₃ | H | OCH₃ | 123–129 d |
| H | CH₂CH₃ | CH₂CH₂CH₃ | H | OCH₃ | |
| H | CH₂CH₃ | OCH₃ | H | OCH₃ | |
| H | CH₂CH₃ | CH₂CH₃ | H | CH₃ | 128–133 d |
| H | CH₂CH₃ | CH₂CH₂CH₃ | H | CH₃ | |
| H | CH₂CH₃ | OCH₃ | H | CH₃ | |
| H | CH₂CH₃ | CH₂CH₃ | H | Cl | 129–130 d |
| H | CH₂CH₃ | CH₂CH₂CH₃ | H | Cl | |
| H | CH₂CH₃ | OCH₃ | H | Cl | |
| H | CH₂CH₃ | CH₂CH₃ | H | CH₂F | |
| H | CH₂CH₃ | CH₂CH₃ | H | OCF₂H | |
| H | CH₂CH₃ | CH₂CH₃ | H | OCH₂CH₃ | |
| H | CH₂CH₃ | CH₂CH₃ | H | CH₂OCH₃ | |
| CH₃ | CH₂CH₃ | CH₂CH₃ | H | OCH₃ | |
| CH₃ | CH₂CH₃ | CH₂CH₃ | H | CH₃ | |
| CH₃ | CH₂CH₃ | CH₂CH₃ | H | Cl | |
| H | CH₂CH₂CH₃ | CH₂CH₂CH₃ | H | OCH₃ | |
| H | CH₂CH₂CH₃ | OCH₃ | H | OCH₃ | |
| H | CH₂CH₂CH₃ | CH₂CH₂CH₃ | H | CH₃ | |
| H | CH₂CH₂CH₃ | OCH₃ | H | CH₃ | |
| H | CH₂CH₂CH₃ | CH₂CH₂CH₃ | H | Cl | |
| H | CH₂CH₂CH₃ | OCH₃ | H | Cl | |
| H | CH(CH₃)₂ | CH(CH₃)₂ | H | OCH₃ | 146–162 d |
| H | H | CH₃ | 4-Cl | OCH₃ | |
| H | H | OCH₃ | 4-Cl | OCH₃ | |
| H | H | CH₃ | 5-Cl | OCH₃ | |
| H | H | OCH₃ | 5-Cl | OCH₃ | |
| H | H | CH₃ | 6-Cl | OCH₃ | |
| H | H | OCH₃ | 6-Cl | OCH₃ | |
| CH₃ | H | CH₃ | 6-Cl | OCH₃ | |
| H | CH₃ | CH₃ | 4-Cl | OCH₃ | |
| H | CH₃ | OCH₃ | 4-Cl | OCH₃ | |
| H | CH₃ | CH₃ | 5-Cl | OCH₃ | |
| H | CH₃ | OCH₃ | 5-Cl | OCH₃ | |
| H | CH₃ | CH₃ | 6-Cl | OCH₃ | |
| H | CH₃ | OCH₃ | 6-Cl | OCH₃ | |
| CH₃ | CH₃ | CH₃ | 6-Cl | OCH₃ | |
| H | CH₃ | CH₃ | 4-Br | OCH₃ | |
| H | CH₃ | CH₃ | 5-Br | OCH₃ | |
| H | CH₃ | CH₃ | 6-Br | OCH₃ | |
| H | CH₃ | CH₃ | 4-F | OCH₃ | |
| H | CH₃ | CH₃ | 5-F | OCH₃ | |
| H | CH₃ | CH₃ | 6-F | OCH₃ | |
| H | CH₃ | CH₃ | 4-CH₃ | OCH₃ | |
| H | CH₃ | CH₃ | 5-CH₃ | OCH₃ | |
| H | CH₃ | CH₃ | 6-CH₃ | OCH₃ | 124–125 d |
| H | CH₃ | CH₃ | 6-CH₃ | CH₃ | 151–153 |
| H | CH₃ | CH₃ | 4-OCH₃ | OCH₃ | |
| H | CH₃ | CH₃ | 5-OCH₃ | OCH₃ | |
| H | CH₃ | CH₃ | 6-OCH₃ | OCH₃ | |
| H | CH₃ | CH₃ | 6-OCH₃ | CH₃ | |
| H | CH₃ | CH₃ | 4-CF₃ | OCH₃ | |
| H | CH₃ | CH₃ | 5-CF₃ | OCH₃ | |

TABLE 1-continued

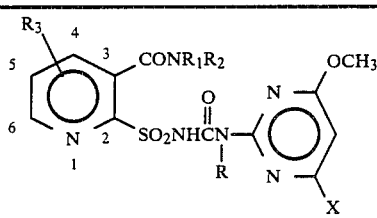

| R | R₁ | R₂ | R₃ | X | m.p. (°C.) |
|---|---|---|---|---|---|
| H | CH₃ | CH₃ | 6-CF₃ | OCH₃ | |
| H | CH₃ | CH₃ | 4-OCF₂H | OCH₃ | |
| H | CH₃ | CH₃ | 5-OCF₂H | OCH₃ | |
| H | CH₃ | CH₃ | 6-OCF₂H | OCH₃ | |
| H | —(CH₂)₂— | | H | OCH₃ | |
| H | —(CH₂)₃— | | H | OCH₃ | |
| H | —(CH₂)₄— | | H | OCH₃ | |

TABLE 2

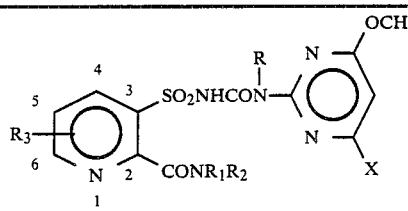

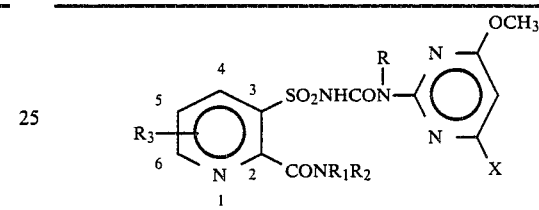

| R | R₁ | R₂ | R₃ | X | m.p. (°C.) |
|---|---|---|---|---|---|
| H | H | CH₃ | H | OCH₃ | |
| H | H | CH₂CH₃ | H | OCH₃ | |
| H | H | CH₂CH₂CH₃ | H | OCH₃ | |
| H | H | CH(CH₃)₂ | H | OCH₃ | |
| H | H | OCH₃ | H | OCH₃ | |
| H | H | OCH₂CH₃ | H | OCH₃ | |
| H | H | CH₃ | H | CH₃ | |
| H | H | CH₂CH₃ | H | CH₃ | |
| H | H | CH₂CH₂CH₃ | H | CH₃ | |
| H | H | CH(CH₃)₂ | H | CH₃ | |
| H | H | OCH₃ | H | CH₃ | |
| H | H | OCH₂CH₃ | H | CH₃ | |
| H | H | CH₃ | H | Cl | |
| H | H | CH₂CH₃ | H | Cl | |
| H | H | CH₂CH₂CH₃ | H | Cl | |
| H | H | CH(CH₃)₂ | H | Cl | |
| H | H | OCH₃ | H | Cl | |
| H | H | OCH₂CH₃ | H | Cl | |
| H | H | CH₃ | H | CH₂F | |
| H | H | CH₂CH₃ | H | CH₂F | |
| H | H | OCH₃ | H | CH₂F | |
| H | H | CH₃ | H | OCF₂H | |
| H | H | CH₂CH₃ | H | OCF₂H | |
| H | H | OCH₃ | H | OCF₂H | |
| H | H | CH₃ | H | OCH₂CH₃ | |
| H | H | CH₂CH₃ | H | OCH₂CH₃ | |
| H | H | OCH₃ | H | OCH₂CH₃ | |
| H | H | CH₃ | H | CH₂OCH₃ | |
| H | H | CH₂CH₃ | H | CH₂OCH₃ | |
| H | H | OCH₃ | H | CH₂OCH₃ | |
| CH₃ | H | CH₃ | H | OCH₃ | |
| CH₃ | H | OCH₃ | H | OCH₃ | |
| CH₃ | H | CH₃ | H | CH₃ | |
| CH₃ | H | OCH₃ | H | CH₃ | |
| CH₃ | H | CH₃ | H | Cl | |
| CH₃ | H | OCH₃ | H | Cl | |
| CH₃ | H | CH₃ | H | CH₂F | |
| CH₃ | H | CH₃ | H | OCF₂H | |
| CH₃ | H | CH₃ | H | CH₂OCH₃ | |
| H | CH₃ | CH₃ | H | OCH₃ | |
| H | CH₃ | CH₂CH₃ | H | OCH₃ | |
| H | CH₃ | CH₂CH₂CH₃ | H | OCH₃ | |
| H | CH₃ | CH(CH₃)₂ | H | OCH₃ | |
| H | CH₃ | OCH₃ | H | OCH₃ | |
| H | CH₃ | OCH₂CH₃ | H | OCH₃ | |
| H | CH₃ | CH₃ | H | CH₃ | |
| H | CH₃ | CH₂CH₃ | H | CH₃ | |
| H | CH₃ | CH₂CH₂CH₃ | H | CH₃ | |
| H | CH₃ | CH(CH₃)₂ | H | CH₃ | |
| H | CH₃ | OCH₃ | H | CH₃ | |
| H | CH₃ | OCH₂CH₃ | H | CH₃ | |
| H | CH₃ | CH₃ | H | Cl | |
| H | CH₃ | CH₂CH₃ | H | Cl | |
| H | CH₃ | CH₂CH₂CH₃ | H | Cl | |
| H | CH₃ | CH(CH₃)₂ | H | Cl | |
| H | CH₃ | OCH₃ | H | Cl | |
| H | CH₃ | OCH₂CH₃ | H | Cl | |
| H | CH₃ | CH₃ | H | CH₂F | |
| H | CH₃ | CH₂CH₃ | H | CH₂F | |
| H | CH₃ | OCH₃ | H | CH₂F | |
| H | CH₃ | CH₃ | H | OCF₂H | |
| H | CH₃ | CH₂CH₃ | H | OCF₂H | |
| H | CH₃ | OCH₃ | H | OCF₂H | |
| H | CH₃ | CH₃ | H | OCH₂CH₃ | |
| H | CH₃ | CH₂CH₃ | H | OCH₂CH₃ | |
| H | CH₃ | CH₃ | H | CH₂OCH₃ | |
| H | CH₃ | CH₂CH₃ | H | CH₂OCH₃ | |
| H | CH₃ | OCH₃ | H | CH₂OCH₃ | |
| CH₃ | CH₃ | CH₃ | H | OCH₃ | |
| CH₃ | CH₃ | OCH₃ | H | OCH₃ | |
| CH₃ | CH₃ | CH₃ | H | CH₃ | |
| CH₃ | CH₃ | OCH₃ | H | CH₃ | |
| CH₃ | CH₃ | CH₃ | H | Cl | |
| CH₃ | CH₃ | OCH₃ | H | Cl | |
| CH₃ | CH₃ | CH₃ | H | CH₂F | |
| CH₃ | CH₃ | CH₃ | H | OCF₂H | |
| CH₃ | CH₃ | CH₃ | H | CH₂OCH₃ | |
| H | CH₂CH₃ | CH₂CH₃ | H | OCH₃ | |
| H | CH₂CH₃ | CH₂CH₂CH₃ | H | OCH₃ | |
| H | CH₂CH₃ | OCH₃ | H | OCH₃ | |
| H | CH₂CH₃ | CH₂CH₃ | H | CH₃ | |
| H | CH₂CH₃ | CH₂CH₂CH₃ | H | CH₃ | |
| H | CH₂CH₃ | OCH₃ | H | CH₃ | |
| H | CH₂CH₃ | CH₂CH₃ | H | Cl | |
| H | CH₂CH₃ | CH₂CH₂CH₃ | H | Cl | |
| H | CH₂CH₃ | OCH₃ | H | Cl | |
| H | CH₂CH₃ | CH₂CH₃ | H | CH₂F | |
| H | CH₂CH₃ | CH₂CH₃ | H | OCF₂H | |
| H | CH₂CH₃ | CH₂CH₃ | H | OCH₂CH₃ | |
| H | CH₂CH₃ | CH₂CH₃ | H | CH₂OCH₃ | |
| CH₃ | CH₂CH₃ | CH₂CH₃ | H | OCH₃ | |

TABLE 2-continued

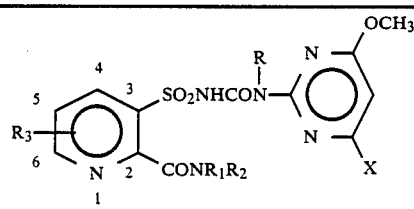

| R | R₁ | R₂ | R₃ | X | m.p. (°C.) |
|---|---|---|---|---|---|
| CH₃ | CH₂CH₃ | CH₂CH₃ | H | CH₃ | |
| CH₃ | CH₂CH₃ | CH₂CH₃ | H | Cl | |
| H | CH₂CH₂CH₃ | CH₂CH₂CH₃ | H | OCH₃ | |
| H | CH₂CH₂CH₃ | OCH₃ | H | OCH₃ | |
| H | CH₂CH₂CH₃ | CH₂CH₂CH₃ | H | CH₃ | |
| H | CH₂CH₂CH₃ | OCH₃ | H | CH₃ | |
| H | CH₂CH₂CH₃ | CH₂CH₂CH₃ | H | Cl | |
| H | CH₂CH₂CH₃ | OCH₃ | H | Cl | |
| H | CH(CH₃)₂ | CH(CH₃)₂ | H | OCH₃ | |
| H | H | CH₃ | 4-Cl | OCH₃ | |
| H | H | OCH₃ | 4-Cl | OCH₃ | |
| H | H | CH₃ | 5-Cl | OCH₃ | |
| H | H | OCH₃ | 5-Cl | OCH₃ | |
| H | H | CH₃ | 6-Cl | OCH₃ | |
| H | H | OCH₃ | 6-Cl | OCH₃ | |
| CH₃ | H | CH₃ | 4-Cl | OCH₃ | |
| H | CH₃ | CH₃ | 4-Cl | OCH₃ | |
| H | CH₃ | OCH₃ | 4-Cl | OCH₃ | |
| H | CH₃ | CH₃ | 5-Cl | OCH₃ | |
| H | CH₃ | OCH₃ | 5-Cl | OCH₃ | |
| H | CH₃ | CH₃ | 6-Cl | OCH₃ | |
| H | CH₃ | OCH₃ | 6-Cl | OCH₃ | |
| CH₃ | CH₃ | CH₃ | 4-Cl | OCH₃ | |
| H | CH₃ | CH₃ | 4-Br | OCH₃ | |
| H | CH₃ | CH₃ | 5-Br | OCH₃ | |
| H | CH₃ | CH₃ | 6-Br | OCH₃ | |
| H | CH₃ | CH₃ | 4-F | OCH₃ | |
| H | CH₃ | CH₃ | 5-F | OCH₃ | |
| H | CH₃ | CH₃ | 6-F | OCH₃ | |
| H | CH₃ | CH₃ | 4-CH₃ | OCH₃ | |
| H | CH₃ | CH₃ | 5-CH₃ | OCH₃ | |
| H | CH₃ | CH₃ | 6-CH₃ | OCH₃ | |
| H | CH₃ | CH₃ | 6-CH₃ | CH₃ | |
| H | CH₃ | CH₃ | 4-OCH₃ | OCH₃ | |
| H | CH₃ | CH₃ | 5-OCH₃ | OCH₃ | |
| H | CH₃ | CH₃ | 6-OCH₃ | OCH₃ | |
| H | CH₃ | CH₃ | 6-OCH₃ | CH₃ | |
| H | CH₃ | CH₃ | 4-CF₃ | OCH₃ | |
| H | CH₃ | CH₃ | 5-CF₃ | OCH₃ | |
| H | CH₃ | CH₃ | 6-CF₃ | OCH₃ | |
| H | CH₃ | CH₃ | 4-OCF₂H | OCH₃ | |
| H | CH₃ | CH₃ | 5-OCF₂H | OCH₃ | |
| H | CH₃ | CH₃ | 6-OCF₂H | OCH₃ | |
| H | —(CH₂)₂— | | H | OCH₃ | |
| H | —(CH₂)₃— | | H | OCH₃ | |
| H | —(CH₂)₄— | | H | OCH₃ | |

TABLE 3

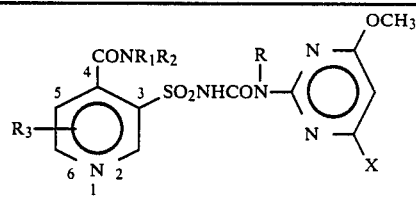

| R | R₁ | R₂ | R₃ | X | m.p. (°C.) |
|---|---|---|---|---|---|
| H | H | CH₃ | H | OCH₃ | |
| H | H | CH₂CH₃ | H | OCH₃ | |
| H | H | CH₂CH₂CH₃ | H | OCH₃ | |
| H | H | CH(CH₃)₂ | H | OCH₃ | |
| H | H | OCH₃ | H | OCH₃ | |
| H | H | OCH₂CH₃ | H | OCH₃ | |
| H | H | CH₃ | H | CH₃ | |

TABLE 3-continued

| R | R₁ | R₂ | R₃ | X | m.p. (°C.) |
|---|---|---|---|---|---|
| H | H | CH₂CH₃ | H | CH₃ | |
| H | H | CH₂CH₂CH₃ | H | CH₃ | |
| H | H | CH(CH₃)₂ | H | CH₃ | |
| H | H | OCH₃ | H | CH₃ | |
| H | H | OCH₂CH₃ | H | CH₃ | |
| H | H | CH₃ | H | Cl | |
| H | H | CH₂CH₃ | H | Cl | |
| H | H | CH₂CH₂CH₃ | H | Cl | |
| H | H | CH(CH₃)₂ | H | Cl | |
| H | H | OCH₃ | H | Cl | |
| H | H | OCH₂CH₃ | H | Cl | |
| H | H | CH₃ | H | CH₂F | |
| H | H | CH₂CH₃ | H | CH₂F | |
| H | H | OCH₃ | H | CH₂F | |
| H | H | CH₃ | H | OCF₂H | |
| H | H | CH₂CH₃ | H | OCF₂H | |
| H | H | OCH₃ | H | OCF₂H | |
| H | H | CH₃ | H | OCH₂CH₃ | |
| H | H | CH₂CH₃ | H | OCH₂CH₃ | |
| H | H | OCH₃ | H | OCH₂CH₃ | |
| H | H | CH₃ | H | CH₂OCH₃ | |
| H | H | CH₂CH₃ | H | CH₂OCH₃ | |
| H | H | OCH₃ | H | CH₂OCH₃ | |
| CH₃ | H | CH₃ | H | OCH₃ | |
| CH₃ | H | OCH₃ | H | OCH₃ | |
| CH₃ | H | CH₃ | H | CH₃ | |
| CH₃ | H | OCH₃ | H | CH₃ | |
| CH₃ | H | CH₃ | H | Cl | |
| CH₃ | H | OCH₃ | H | Cl | |
| CH₃ | H | CH₃ | H | CH₂F | |
| CH₃ | H | CH₃ | H | OCF₂H | |
| CH₃ | H | CH₃ | H | CH₂OCH₃ | |
| H | CH₃ | CH₃ | H | OCH₃ | 202–204 d |
| H | CH₃ | CH₂CH₃ | H | OCH₃ | |
| H | CH₃ | CH₂CH₂CH₃ | H | OCH₃ | |
| H | CH₃ | CH(CH₃)₂ | H | OCH₃ | |
| H | CH₃ | OCH₃ | H | OCH₃ | |
| H | CH₃ | OCH₂CH₃ | H | OCH₃ | |
| H | CH₃ | CH₃ | H | CH₃ | |
| H | CH₃ | CH₂CH₃ | H | CH₃ | |
| H | CH₃ | CH₂CH₂CH₃ | H | CH₃ | |
| H | CH₃ | CH(CH₃)₂ | H | CH₃ | |
| H | CH₃ | OCH₃ | H | CH₃ | |
| H | CH₃ | OCH₂CH₃ | H | CH₃ | |
| H | CH₃ | CH₃ | H | Cl | |
| H | CH₃ | CH₂CH₃ | H | Cl | |
| H | CH₃ | CH₂CH₂CH₃ | H | Cl | |
| H | CH₃ | CH(CH₃)₂ | H | Cl | |
| H | CH₃ | OCH₃ | H | Cl | |
| H | CH₃ | OCH₂CH₃ | H | Cl | |
| H | CH₃ | CH₃ | H | CH₂F | |
| H | CH₃ | CH₂CH₃ | H | CH₂F | |
| H | CH₃ | OCH₃ | H | CH₂F | |
| H | CH₃ | CH₃ | H | OCF₂H | |
| H | CH₃ | CH₂CH₃ | H | OCF₂H | |
| H | CH₃ | OCH₃ | H | OCF₂H | |
| H | CH₃ | CH₃ | H | OCH₂CH₃ | |
| H | CH₃ | CH₂CH₃ | H | OCH₂CH₃ | |
| H | CH₃ | OCH₃ | H | OCH₂CH₃ | |
| H | CH₃ | CH₃ | H | CH₂OCH₃ | |
| H | CH₃ | CH₂CH₃ | H | CH₂OCH₃ | |
| H | CH₃ | OCH₃ | H | CH₂OCH₃ | |
| CH₃ | CH₃ | CH₃ | H | OCH₃ | |
| CH₃ | CH₃ | OCH₃ | H | OCH₃ | |
| CH₃ | CH₃ | CH₃ | H | CH₃ | |
| CH₃ | CH₃ | OCH₃ | H | CH₃ | |
| CH₃ | CH₃ | CH₃ | H | Cl | |
| CH₃ | CH₃ | OCH₃ | H | Cl | |
| CH₃ | CH₃ | CH₃ | H | CH₂F | |

TABLE 3-continued

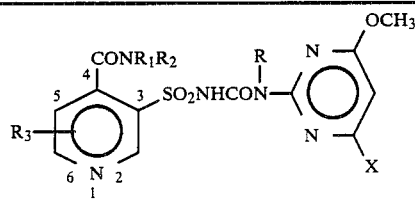

| R | R₁ | R₂ | R₃ | X | m.p. (°C.) |
|---|---|---|---|---|---|
| CH₃ | CH₃ | CH₃ | H | OCF₂H | |
| CH₃ | CH₃ | CH₃ | H | CH₂OCH₃ | |
| H | CH₂CH₃ | CH₂CH₃ | H | OCH₃ | |
| H | CH₂CH₃ | CH₂CH₂CH₃ | H | OCH₃ | |
| H | CH₂CH₃ | OCH₃ | H | OCH₃ | |
| H | CH₂CH₃ | CH₂CH₃ | H | CH₃ | |
| H | CH₂CH₃ | CH₂CH₂CH₃ | H | CH₃ | |
| H | CH₂CH₃ | OCH₃ | H | CH₃ | |
| H | CH₂CH₃ | CH₂CH₃ | H | Cl | |
| H | CH₂CH₃ | CH₂CH₂CH₃ | H | Cl | |
| H | CH₂CH₃ | OCH₃ | H | Cl | |
| H | CH₂CH₃ | CH₂CH₃ | H | CH₂F | |
| H | CH₂CH₃ | CH₂CH₃ | H | OCF₂H | |
| H | CH₂CH₃ | CH₂CH₃ | H | OCH₂CH₃ | |
| H | CH₂CH₃ | CH₂CH₃ | H | CH₂OCH₃ | |
| CH₃ | CH₂CH₃ | CH₂CH₃ | H | OCH₃ | |
| CH₃ | CH₂CH₃ | CH₂CH₃ | H | CH₃ | |
| CH₃ | CH₂CH₃ | CH₂CH₃ | H | Cl | |
| H | CH₂CH₂CH₃ | CH₂CH₂CH₃ | H | OCH₃ | |
| H | CH₂CH₂CH₃ | OCH₃ | H | OCH₃ | |
| H | CH₂CH₂CH₃ | CH₂CH₂CH₃ | H | CH₃ | |
| H | CH₂CH₂CH₃ | OCH₃ | H | CH₃ | |
| H | CH₂CH₂CH₃ | CH₂CH₂CH₃ | H | Cl | |
| H | CH₂CH₂CH₃ | OCH₃ | H | Cl | |
| H | CH(CH₃)₂ | CH(CH₃)₂ | H | OCH₃ | |
| H | H | CH₃ | 2-Cl | OCH₃ | |
| H | H | OCH₃ | 2-Cl | OCH₃ | |
| H | H | CH₃ | 5-Cl | OCH₃ | |
| H | H | OCH₃ | 5-Cl | OCH₃ | |
| H | H | CH₃ | 6-Cl | OCH₃ | |
| H | H | OCH₃ | 6-Cl | OCH₃ | |
| CH₃ | H | CH₃ | 2-Cl | OCH₃ | |
| H | CH₃ | CH₃ | 2-Cl | OCH₃ | |
| H | CH₃ | OCH₃ | 2-Cl | OCH₃ | |
| H | CH₃ | CH₃ | 5-Cl | OCH₃ | |
| H | CH₃ | OCH₃ | 5-Cl | OCH₃ | |
| H | CH₃ | CH₃ | 6-Cl | OCH₃ | |
| H | CH₃ | OCH₃ | 6-Cl | OCH₃ | |
| CH₃ | CH₃ | CH₃ | 2-Cl | OCH₃ | |
| H | CH₃ | CH₃ | 2-Br | OCH₃ | |
| H | CH₃ | CH₃ | 5-Br | OCH₃ | |
| H | CH₃ | CH₃ | 6-Br | OCH₃ | |
| H | CH₃ | CH₃ | 2-F | OCH₃ | |
| H | CH₃ | CH₃ | 5-F | OCH₃ | |
| H | CH₃ | CH₃ | 6-F | OCH₃ | |
| H | CH₃ | CH₃ | 2-CH₃ | OCH₃ | |
| H | CH₃ | CH₃ | 5-CH₃ | OCH₃ | |
| H | CH₃ | CH₃ | 6-CH₃ | OCH₃ | |
| H | CH₃ | CH₃ | 6-CH₃ | CH₃ | |
| H | CH₃ | CH₃ | 2-OCH₃ | OCH₃ | |
| H | CH₃ | CH₃ | 5-OCH₃ | OCH₃ | |
| H | CH₃ | CH₃ | 6-OCH₃ | OCH₃ | |
| H | CH₃ | CH₃ | 6-OCH₃ | CH₃ | |
| H | CH₃ | CH₃ | 2-CF₃ | OCH₃ | |
| H | CH₃ | CH₃ | 5-CF₃ | OCH₃ | |
| H | CH₃ | CH₃ | 6-CF₃ | OCH₃ | |
| H | CH₃ | CH₃ | 2-OCF₂H | OCH₃ | |
| H | CH₃ | CH₃ | 5-OCF₂H | OCH₃ | |
| H | CH₃ | CH₃ | 6-OCF₂H | OCH₃ | |
| H | —(CH₂)₂— | | H | OCH₃ | |
| H | —(CH₂)₃— | | H | OCH₃ | |
| H | —(CH₂)₄— | | H | OCH₃ | |

TABLE 4

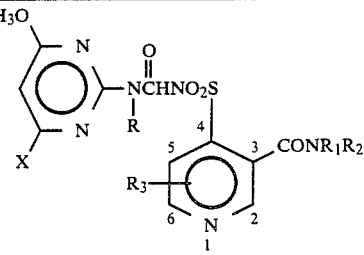

| R | R₁ | R₂ | R₃ | X | m.p. (°C.) |
|---|---|---|---|---|---|
| H | H | CH₃ | H | OCH₃ | |
| H | H | CH₂CH₃ | H | OCH₃ | |
| H | H | CH₂CH₂CH₃ | H | OCH₃ | |
| H | H | CH(CH₃)₂ | H | OCH₃ | |
| H | H | OCH₃ | H | OCH₃ | |
| H | H | OCH₂CH₃ | H | OCH₃ | |
| H | H | CH₃ | H | CH₃ | |
| H | H | CH₂CH₃ | H | CH₃ | |
| H | H | CH₂CH₂CH₃ | H | CH₃ | |
| H | H | CH(CH₃)₂ | H | CH₃ | |
| H | H | OCH₃ | H | CH₃ | |
| H | H | OCH₂CH₃ | H | CH₃ | |
| H | H | CH₃ | H | Cl | |
| H | H | CH₂CH₃ | H | Cl | |
| H | H | CH₂CH₂CH₃ | H | Cl | |
| H | H | CH(CH₃)₂ | H | Cl | |
| H | H | OCH₃ | H | Cl | |
| H | H | OCH₂CH₃ | H | Cl | |
| H | H | CH₃ | H | CH₂F | |
| H | H | CH₂CH₃ | H | CH₂F | |
| H | H | OCH₃ | H | CH₂F | |
| H | H | CH₃ | H | OCF₂H | |
| H | H | CH₂CH₃ | H | OCF₂H | |
| H | H | OCH₃ | H | OCF₂H | |
| H | H | CH₃ | H | OCH₂CH₃ | |
| H | H | CH₂CH₃ | H | OCH₂CH₃ | |
| H | H | OCH₃ | H | OCH₂CH₃ | |
| H | H | CH₃ | H | CH₂OCH₃ | |
| H | H | CH₂CH₃ | H | CH₂OCH₃ | |
| H | H | OCH₃ | H | CH₂OCH₃ | |
| CH₃ | H | CH₃ | H | OCH₃ | |
| CH₃ | H | OCH₃ | H | OCH₃ | |
| CH₃ | H | CH₃ | H | CH₃ | |
| CH₃ | H | OCH₃ | H | CH₃ | |
| CH₃ | H | CH₃ | H | Cl | |
| CH₃ | H | OCH₃ | H | Cl | |
| CH₃ | H | CH₃ | H | CH₂F | |
| CH₃ | H | CH₃ | H | OCF₂H | |
| CH₃ | H | CH₃ | H | CH₂OCH₃ | |
| H | CH₃ | CH₃ | H | OCH₃ | |
| H | CH₃ | CH₂CH₃ | H | OCH₃ | |
| H | CH₃ | CH₂CH₂CH₃ | H | OCH₃ | |
| H | CH₃ | CH(CH₃)₂ | H | OCH₃ | |
| H | CH₃ | OCH₃ | H | OCH₃ | |
| H | CH₃ | OCH₂CH₃ | H | OCH₃ | |
| H | CH₃ | CH₃ | H | CH₃ | |
| H | CH₃ | CH₂CH₃ | H | CH₃ | |
| H | CH₃ | CH₂CH₂CH₃ | H | CH₃ | |
| H | CH₃ | CH(CH₃)₂ | H | CH₃ | |
| H | CH₃ | OCH₃ | H | CH₃ | |
| H | CH₃ | OCH₂CH₃ | H | CH₃ | |
| H | CH₃ | CH₃ | H | Cl | |
| H | CH₃ | CH₂CH₃ | H | Cl | |
| H | CH₃ | CH₂CH₂CH₃ | H | Cl | |
| H | CH₃ | CH(CH₃)₂ | H | Cl | |
| H | CH₃ | OCH₃ | H | Cl | |
| H | CH₃ | OCH₂CH₃ | H | Cl | |
| H | CH₃ | CH₃ | H | CH₂F | |
| H | CH₃ | CH₂CH₃ | H | CH₂F | |
| H | CH₃ | OCH₃ | H | CH₂F | |
| H | CH₃ | CH₃ | H | OCF₂H | |
| H | CH₃ | CH₂CH₃ | H | OCF₂H | |
| H | CH₃ | OCH₃ | H | OCF₂H | |
| H | CH₃ | CH₃ | H | OCH₂CH₃ | |
| H | CH₃ | CH₂CH₃ | H | OCH₂CH₃ | |
| H | CH₃ | OCH₃ | H | OCH₂CH₃ | |
| H | CH₃ | CH₃ | H | CH₂OCH₃ | |

TABLE 4-continued

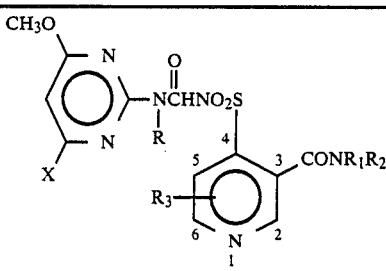

| R | R₁ | R₂ | R₃ | X | m.p. (°C.) |
|---|---|---|---|---|---|
| H | CH₃ | CH₂CH₃ | H | CH₂OCH₃ | |
| H | CH₃ | OCH₃ | H | CH₂OCH₃ | |
| CH₃ | CH₃ | CH₃ | H | OCH₃ | |
| CH₃ | CH₃ | OCH₃ | H | OCH₃ | |
| CH₃ | CH₃ | CH₃ | H | CH₃ | |
| CH₃ | CH₃ | OCH₃ | H | CH₃ | |
| CH₃ | CH₃ | CH₃ | H | Cl | |
| CH₃ | CH₃ | OCH₃ | H | Cl | |
| CH₃ | CH₃ | CH₃ | H | CH₂F | |
| CH₃ | CH₃ | CH₃ | H | OCF₂H | |
| CH₃ | CH₃ | CH₃ | H | CH₂OCH₃ | |
| H | CH₂CH₃ | CH₂CH₃ | H | OCH₃ | |
| H | CH₂CH₃ | CH₂CH₂CH₃ | H | OCH₃ | |
| H | CH₂CH₃ | OCH₃ | H | OCH₃ | |
| H | CH₂CH₃ | CH₂CH₃ | H | CH₃ | |
| H | CH₂CH₃ | CH₂CH₂CH₃ | H | CH₃ | |
| H | CH₂CH₃ | OCH₃ | H | CH₃ | |
| H | CH₂CH₃ | CH₂CH₃ | H | Cl | |
| H | CH₂CH₃ | CH₂CH₂CH₃ | H | Cl | |
| H | CH₂CH₃ | OCH₃ | H | Cl | |
| H | CH₂CH₃ | CH₂CH₃ | H | CH₂F | |
| H | CH₂CH₃ | CH₂CH₃ | H | OCF₂H | |
| H | CH₂CH₃ | CH₂CH₃ | H | OCH₂CH₃ | |
| H | CH₂CH₃ | CH₂CH₃ | H | CH₂OCH₃ | |
| CH₃ | CH₂CH₃ | CH₂CH₃ | H | OCH₃ | |
| CH₃ | CH₂CH₃ | CH₂CH₃ | H | CH₃ | |
| CH₃ | CH₂CH₃ | CH₂CH₃ | H | Cl | |
| H | CH₂CH₂CH₃ | CH₂CH₂CH₃ | H | OCH₃ | |
| H | CH₂CH₂CH₃ | OCH₃ | H | OCH₃ | |
| H | CH₂CH₂CH₃ | CH₂CH₂CH₃ | H | CH₃ | |
| H | CH₂CH₂CH₃ | OCH₃ | H | CH₃ | |
| H | CH₂CH₂CH₃ | CH₂CH₂CH₃ | H | Cl | |
| H | CH₂CH₂CH₃ | OCH₃ | H | Cl | |
| H | CH(CH₃)₂ | CH(CH₃)₂ | H | OCH₃ | |
| H | H | CH₃ | 2-Cl | OCH₃ | |
| H | H | OCH₃ | 2-Cl | OCH₃ | |
| H | H | CH₃ | 5-Cl | OCH₃ | |
| H | H | OCH₃ | 5-Cl | OCH₃ | |
| H | H | CH₃ | 6-Cl | OCH₃ | |
| H | H | OCH₃ | 6-Cl | OCH₃ | |
| CH₃ | H | CH₃ | 2-Cl | OCH₃ | |
| H | CH₃ | CH₃ | 2-Cl | OCH₃ | |
| H | CH₃ | OCH₃ | 2-Cl | OCH₃ | |
| H | CH₃ | CH₃ | 5-Cl | OCH₃ | |
| H | CH₃ | OCH₃ | 5-Cl | OCH₃ | |
| H | CH₃ | CH₃ | 6-Cl | OCH₃ | |
| H | CH₃ | OCH₃ | 6-Cl | OCH₃ | |
| CH₃ | CH₃ | CH₃ | 2-Cl | OCH₃ | |
| H | CH₃ | CH₃ | 2-Br | OCH₃ | |
| H | CH₃ | CH₃ | 5-Br | OCH₃ | |
| H | CH₃ | CH₃ | 6-Br | OCH₃ | |
| H | CH₃ | CH₃ | 2-F | OCH₃ | |
| H | CH₃ | CH₃ | 5-F | OCH₃ | |
| H | CH₃ | CH₃ | 6-F | OCH₃ | |
| H | CH₃ | CH₃ | 2-CH₃ | OCH₃ | |
| H | CH₃ | CH₃ | 5-CH₃ | OCH₃ | |
| H | CH₃ | CH₃ | 6-CH₃ | OCH₃ | |
| H | CH₃ | CH₃ | 6-CH₃ | CH₃ | |
| H | CH₃ | CH₃ | 2-OCH₃ | OCH₃ | |
| H | CH₃ | CH₃ | 5-OCH₃ | OCH₃ | |
| H | CH₃ | CH₃ | 6-OCH₃ | OCH₃ | |
| H | CH₃ | CH₃ | 6-OCH₃ | CH₃ | |
| H | CH₃ | CH₃ | 2-CF₃ | OCH₃ | |
| H | CH₃ | CH₃ | 5-CF₃ | OCH₃ | |
| H | CH₃ | CH₃ | 6-CF₃ | OCH₃ | |
| H | CH₃ | CH₃ | 2-OCF₂H | OCH₃ | |
| H | CH₃ | CH₃ | 5-OCF₂H | OCH₃ | |

TABLE 4-continued

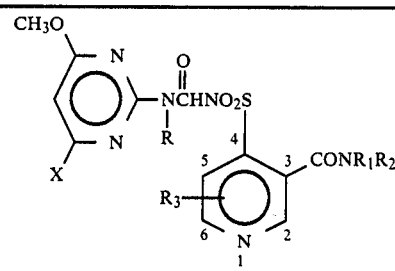

| R | R₁ | R₂ | R₃ | X | m.p. (°C.) |
|---|---|---|---|---|---|
| H | CH₃ | CH₃ | 6-OCF₂H | OCH₃ | |
| H | | —(CH₂)₂— | H | OCH₃ | |
| H | | —(CH₂)₃— | H | OCH₃ | |
| H | | —(CH₂)₄— | H | OCH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Active Ingredient | Weight Percent* Diluent(s) | Surfactant(s) |
|---|---|---|---|
| Wettable powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, and the like.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See Browning, "Agglomeration", *Chemical Engineering*, Dec. 4, 1967, pp. 147ff. and "Perry's Chemical Engineer's Handbook", 5th Ed., McGraw-Hill New York, 1973, pages 8 to 57 and following.

For further information regarding the art of formulation, see for example: U.S. Pat. No. 3,235,361, column 6, line 16 through column 7, line 19 and Examples 10 through 41; U.S. Pat. No. 3,309,192, column 5, line 43 through column 7, line 62 and Examples 8, 12, 15, 39, 41, 52, 53, 58, 132, 138 to 140, 162 to 164, 166, 167 and 169 to 182; U.S. Pat. No. 2,891,855, column 3, line 66 through column 5, line 17 and Examples 1 to 4; Klingman, "Weed Control as a Science", John Wiley and Sons, Inc., New York, 1961, pages 81 to 96; and Fryer et al., "Weed Control Handbook", 5th Ed., Blackwell Scientific Publications, Oxford, 1968, pages 101 to 103.

In the following Examples, all parts are by weight unless otherwise indicated.

EXAMPLE 10

Wettable Powder

| | |
|---|---|
| 2-[[(4,6-dimethoxypyrimidin-2-yl)aminocarbonyl]aminosulfonyl]-N,N—dimethyl-3-pyridinecarboxamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

Granule

| | |
|---|---|
| Wettable Powder of Example 10 | 5% |
| attapulgite granules (U.S.S. 20 to 40 mesh; 0.84 to 0.42 mm) | 95% |

A slurry of wettable powder containing 25% solids is sprayed on the surface of attapulgite granules in a double-cone blender. The granules are dried and packaged.

EXAMPLE 12

Extruded Pellet

| | |
|---|---|
| 2-[[(4,6-dimethoxypyrimidin-2-yl)aminocarbonyl]aminosulfonyl]-N,N—dimethyl-3-pyridinecarboxamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Low Strength Granule

| | |
|---|---|
| 2-[[(4,6-dimethoxypyrimidin-2-yl)aminocarbonyl]aminosulfonyl]-N,N—dimethyl-3-pyridinecarboxamide | 1% |
| N,N—dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

Aqueous Suspension

| | |
|---|---|
| 2-[[(4,6-dimethoxypyrimidin-2-yl)aminocarbonyl]aminosulfonyl]-N,N—dimethyl-3-pyridinecarboxamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

Oil Suspension

| | |
|---|---|
| 2-[[(4,6-dimethoxypyrimidin-2-yl)aminocarbonyl]aminosulfonyl]-N,N—dimethyl-3-pyridinecarboxamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 16

Granule

| | |
|---|---|
| 2-[[(4,6-dimethoxypyrimidin-2-yl)aminocarbonyl]aminosulfonyl]-N,N—dimethyl-3-pyridinecarboxamide | 80% |
| wetting agent | 1% |
| crude ligninsulfonate salt (containing 5 to 20% of the natural sugars) | 10% |

| | |
|---|---|
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 17

High Strength Concentrate

| | |
|---|---|
| 2-[[(4,6-dimethoxypyrimidin-2-yl)aminocarbonyl]aminosulfonyl]-N,N—dimethyl-3-pyridinecarboxamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 18

Wettable Powder

| | |
|---|---|
| 2-[[(4,6-dimethoxypyrimidin-2-yl)aminocarbonyl]aminosulfonyl]-N,N—dimethyl-3-pyridinecarboxamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 19

Wettable Powder

| | |
|---|---|
| 2-[[(4,6-dimethoxypyrimidin-2-yl)aminocarbonyl]aminosulfonyl]-N,N—dimethyl-3-pyridinecarboxamide | 20% |
| sodium ligninsulfonate | 20% |
| montmorillonite clay | 60% |

The ingredients are thoroughly blended, coarsely hammer-milled and then air-milled to produce particles essentially all below 10 microns in size. The material is reblended and then packaged.

EXAMPLE 20

Dust

| | |
|---|---|
| 2-[[(4,6-dimethoxypyrimidin-2-yl)aminocarbonyl]aminosulfonyl]-N,N—dimethyl-3-pyridinecarboxamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Corn (maize) is a very important cereal crop, providing animal feed as well as food for human consumption. As with all crops, high yields depend on good control of unwanted plants to minimize competitive effects on the crop. Since corn is a grass, it is particularly difficult to control other grasses competing with the crop. The compounds of this invention control weeds in corn both pre- and postemergence without significant crop damage. They are particularly useful to control such problem weeds as the foxtail (Setaria spp.), fall panicum (*Panicum dichotomiflorum*), barnyardgrass (*Echinochloa crusgallis*), seedling johnsongrass (*Sorghum halepense*) and shattercane (*Sorghum bicolor*). They can be used preemergence or postemergence and are most effective when applied postemergence to young weeds. They are also effective on certain broadleaf weeds such as lambsquarter (*Chenopodium album*), pigweed (*Amaranthus* spp.) and jimsonweed (*Datura stramonium*). The rate used can vary from about 1 g/ha to 1000 g/ha depending on the number and age of weeds present, soil type, climate, formulation used and method of application. One of ordinary skill in the art can readily select the exact rate and method of application that will provide the desired herbicidal efficacy.

The compounds of this invention may be used in combination with other commercial herbicides. They are particularly useful in combination with the following herbicides.

| Common Name | Chemical Name |
|---|---|
| alachlor | 2 chloro-2',6'-diethyl-N—(methoxymethyl)-acetanilide |
| atrazine | 2-chloro-4-(ethylamino)-6-(isopropylamino)-s-triazine |
| butylate | S—ethyl-diisobutylthiocarbamate |
| cyanazine | 2-[[4-chloro-6-(ethylamino)-s-triazin-2-yl]amino]-2-methylpropionitrile |
| dicamba | 3,6-dichloro-o-anisic acid |
| EPTC | S—ethyl dipropylthiocarbamate |
| linuron | 3-(3,4-dichlorophenyl)-1-methoxy-1-methylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)-one |
| tridiphane | 2-(3,5-dichlorophenyl)-2-(2,2,2-trichloroethyl)oxirane |
| 2,4-D | (2,4-dichlorophenoxy)acetic acid |
| bromoxynil | 3,5-dibromo-4-hydroxyphenylcyanide |
| paraquat | 1,1'-dimethyl-4,4-bipyridinium ion |
| glyphosate | N—(phosphonomethyl)glycine |
| Trade Name | |
| Harmony ™ | 3-[[(4-methoxy-6-methyl-1,3,5-triazin-2-yl)aminocarbonyl]aminosulfonyl]-2-thiophenecarboxylic acid, methyl ester |
| Cinch ® | 1-methyl-4-(1-methylethyl)-2-exo-[(2-methylphenyl)-methoxy]-7-oxabicyclo-[2.2.1]heptane |
| — | 2-ethoxy-N—[[4-(2,2,2-trifluoroethoxy)-6-methoxy-1,3,5-triazin-2-yl]aminocarbonyl]benzenesulfonamide |

The utility of these chemicals is demonstrated in terms of the greenhouse test data summarized hereafter. The results demonstrate the herbicidal efficacy and corn selectivity of the compounds of this invention.

Compounds

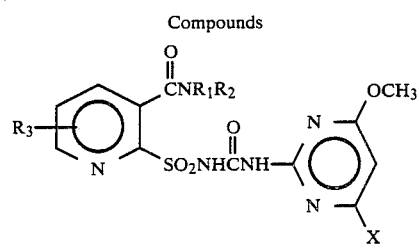

| Compound | R₁ | R₂ | R₃ | X |
|---|---|---|---|---|
| 1 | $CH_3$ | $OCH_3$ | H | $OCH_3$ |
| 2 | $CH_3$ | $OCH_3$ | H | $CH_3$ |
| 3 | $CH_3$ | $CH_3$ | 6-$CH_3$ | $OCH_3$ |
| 4 | $CH_3$ | $CH_3$ | 6-$CH_3$ | $CH_3$ |
| 5 | $CH_3$ | $CH_3$ | H | $OCF_2H$ |
| 6 | $CH_3$ | $CH_2CH_3$ | H | $OCH_3$ |
| 7 | $CH_3$ | $CH_2CH_3$ | H | $CH_3$ |
| 8 | $CH(CH_3)_2$ | $CH(CH_3)_2$ | H | $OCH_3$ |
| 9 | $CH(CH_3)_2$ | $CH(CH_3)_2$ | H | $CH_3$ |
| 10 | $CH_2CH_3$ | $CH_2CH_3$ | H | $OCH_3$ |
| 11 | $CH_3$ | $CH_3$ | H | $CH_3$ |
| 12 | $CH_3$ | $CH_3$ | H | $OCH_3$ |
| 13 | $CH_3$ | $CH_3$ | H | Cl |
| 14 | $CH_2CH_3$ | $CH_2CH_3$ | H | Cl |

Test A

Seeds of crabgrass (Digitaria sp.), barnyardgrass (Echinochloa crusgalli), giant foxtail (Setaria faberi), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| RATE RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.01 | CMPD 8 0.05 | CMPD 8 0.01 | CMPD 9 0.05 | CMPD 9 0.01 | CMPD 10 0.05 | CMPD 10 0.01 |
|---|---|---|---|---|---|---|---|---|---|---|---|---|---|---|---|---|---|---|---|---|
| | | | | | | | POSTEMERGENCE | | | | | | | | | | | | | |
| COTTON | 4C,9G | 4C,8H | 3C,7H | 2G | 5C,9G | 2C,9G | 3C,8H | 0 | 3C,7H | 3C,4G | 4C,9H | 4C,8H | 2G | 0 | 1C | — | 3C,5H | — | 4C,8H | — |
| MORNING GLORY | 9C | 4C,9H | 4C,9G | 3C,5H | 10C | 4C,9G | 3C,7H | 1H | 3C,8H | 3C,3H | 4C,9G | 3C,8H | 4C,9H | 3C,5H | 2H | — | 4C,8H | — | 4C,9G | — |
| COCKLEBUR | 10C | 4G | 4C,8H | 2C,2H | 10C | 4C,9H | 3G,7H | 1H | 2C,2H | 3C,2H | 4C,9H | 3C,7H | 2C,5G | 3C,5G | 3C,7H | — | 4C,9H | — | 4C,9H | — |
| NUTSEDGE | 8G | 4C,8G | 3C,8G | 0 | 5C,9G | 4C,9G | 2C,8G | 0 | 3G | 0 | 4C,9H | 3G | 2G | 0 | 3G | — | 2G | — | 4C,9G | — |
| CRABGRASS | 3C,7G | 2G | 3C,5G | 4C,8H | 8G | 10C | 0 | 0 | 3G | 5C,9H | 5G,9G | 3C,7G | 5C,9G | 2C,5H | 0 | — | 0 | — | 0 | — |
| BARNYARD GRASS | 9C | 5C,9H | 9C | 4C,8H | 9C | 3C,6G | 3C,8G | 0 | 9C | 2C,9G | 8G | 9C | 5C,9H | 3C,8H | 9H | — | 3C,8H | — | 3C,6G | — |
| WILD OATS | 6C,9G | 5C,9G | 5C,9G | 4C,9G | 5C,9G | 3C,6G | 2C,7G | 0 | 2C,9G | 2C,9G | 5G | 3C,7G | 4C,9G | 2C,8G | 0 | — | 2C,5G | — | 3C,9G | — |
| WHEAT | 6C,9G | 3C,9G | 9C | 9G | 5C,9G | 9C | 3C,9G | 2G | 9C | 9G | 4C,9G | 9G | 9G | 9G | 0 | — | 4C,9G | — | 2C,6G | — |
| CORN | 0 | 0 | 0 | 0 | 0 | 0 | 0 | 0 | 0 | 0 | 0 | 0 | 0 | 0 | 0 | — | 0 | — | 0 | — |
| SOYBEAN | 4C,9G | 3C,8G | 4C,9G | 3H | 4C,9G | 4C,9G | 2C,6G | 2C,5G | 3C,8H | 3C,3H | 4C,8G | 4C,9G | 3C,8G | 2G | 3C,5H | — | 0 | — | 3C,6G | — |
| RICE | 9C | 9C | 9C | 4C,9G | 9C | 9C | 9C | 2C,6G | 5C,9G | 8G | 9C | 9C | 5C,9G | 5G | 5C,5H | — | 3G | — | 3C,8G | — |
| SORGHUM | 5C,9G | 4C,9G | 3C,9G | 4C,9H | 10C | 10C | 3C,8H | 0 | 3C,8G | 3C,7G | 4C,9G | 10C | 4C,9G | 2G | 2C,9G | — | 9C | — | 10C | — |
| CHEATGRASS | 5C,9G | 2C,9G | 3C,9G | 3C,9G | 9C | 4C,9G | 3C,8G | 0 | 3C,9G | 3C,9G | 10C | 9C | 4C,9G | 5G | 5G | — | 4C,9G | — | 10C | — |
| SUGAR BEETS | 9C | 4C,9G | 4C,9H | 3C,5H | 10C | 4C,8H | 3C,6H | 0 | 3C,6H | 3C,5H | 10C | 5C,9H | 4C,8H | 2G | 3C,7G | — | 2C,8G | — | 9C | — |
| VELVETLEAF | 4C,9H | 4C,8H | 4C,8H | 3C,5G | 9C | 3C,7H | 2C,4G | 0 | 2C,2H | 0 | 4C,9H | 4C,8H | 4C,8H | 7G | 4C,8H | — | 3C,7H | — | 9C | — |
| GIANT FOXTAIL | 9C | 5C,9G | 5C,9G | 4C,9G | 5C,9G | 5C,9G | 3C,8G | 1H | 4C,9H | 3C,6H | 4C,9G | 4C,9G | 4C,9G | 2H | 2C,5G | — | 3C,7G | — | 4C,9H | — |
| BARLEY | 5C,9G | 3C,9G | 3C,9G | 3C,8G | 6C,9G | 5C,9G | 3C,6G | 1C | 5C,9G | 3C,8H | 4C,9G | 4C,9G | 4C,9H | 3C,7G | 3C,5G | — | 3C,9G | — | 4C,9G | — |
| | | | | | | | PREEMERGENCE | | | | | | | | | | | | | |
| COTTON | 8G | 2G | 0 | 0 | 0 | 0 | 0 | 0 | 0 | 0 | 2C,4G | 0 | 0 | 0 | 0 | | | | | |
| MORNING GLORY | 3H | 1H | 3G | 1C | 7H | 0 | 2G | 0 | 3G | 0 | 3C,7H | 0 | 3G | 0 | 0 | | | | | |
| COCKLEBUR | 6H | — | 0 | 0 | 8H | 1H | 0 | 0 | 0 | 0 | 3C,3H | 0 | — | — | — | | | | | |
| NUTSEDGE | 9G | 3C,5G | 0 | 0 | — | 0 | 0 | 0 | 0 | 0 | 9G | 0 | 0 | 0 | 0 | | | | | |
| CRABGRASS | 3G | 0 | 0 | 0 | 9G | 0 | 0 | 0 | 0 | 0 | 3G | 0 | 0 | 0 | 0 | | | | | |
| BARNYARD GRASS | 3C,9H | 2C | 3G | 0 | 2C,2G | 5G | 0 | 0 | 3G | 0 | 9H | 2G | 3G | 0 | 0 | | | | | |
| WILD OATS | 3C,7G | 3G | 3G | 0 | 9H | 2G | 0 | 0 | 0 | 0 | 3C,7G | 3G | 0 | 0 | 0 | | | | | |
| WHEAT | 2C,8G | 3G | 0 | 0 | 2C,6G | 0 | 0 | 0 | 0 | 0 | 3C,9H | 5G | 0 | 0 | 0 | | | | | |
| CORN | 0 | 0 | 0 | 0 | 8G | 2G | 0 | 0 | 0 | 0 | 0 | 2G | 0 | 0 | 0 | | | | | |
| SOYBEAN | 1H | 0 | 0 | 0 | 0 | 0 | 0 | 0 | 0 | 0 | 2C,6H | 2C,6G | 0 | 0 | 0 | | | | | |
| RICE | 9H | 2C,5G | 3G | 1C | 3C,6H | 2G | 0 | 0 | 0 | 0 | 5C,9H | 3C,8H | 0 | 0 | 0 | | | | | |
| SORGHUM | 3C,9H | 3C,8G | 0 | 0 | 9H | 7G | 3C,7H | 0 | 3C,7H | 0 | 4C,9H | 3C,9H | 7G | 0 | 0 | | | | | |
| CHEATGRASS | 2C,8G | 6G | 0 | 0 | 8G | 3C,6G | 0 | 0 | 5G | 2C | 9G | 7G | 5G | 0 | 2C,2G | | | | | |
| SUGAR BEETS | 3C,8G | 3H | 0 | 0 | 4C,9G | 3G | 0 | 0 | 3H | 0 | 4C,9G | 3C,8H | 0 | 0 | 0 | | | | | |
| VELVETLEAF | 7H | 3C,3G | 3G | 1C | 7H | 0 | 0 | 0 | 0 | 0 | 3C,3H | 0 | 4C,8H | 0 | 0 | | | | | |
| GIANT FOXTAIL | 3C,8H | 2G | 2G | 0 | 3C,7G | 0 | 0 | 0 | 0 | 0 | 3C,8H | 0 | 2H | 0 | 0 | | | | | |
| BARLEY | 3C,6G | 0 | 0 | 0 | 9G | 0 | 0 | 0 | 0 | 0 | 9G | 2C,7G | 3C,7G | 0 | 0 | | | | | |

| RATE RATE = KG/HA | CMPD 10 0.01 | CMPD 11 0.05 | CMPD 11 0.01 | CMPD 12 0.05 | CMPD 12 0.01 | CMPD 13 0.05 | CMPD 13 0.01 | CMPD 14 0.05 | CMPD 14 0.01 |
|---|---|---|---|---|---|---|---|---|---|
| | | POSTEMERGENCE | | | | | | | |
| COTTON | — | 2C,6G | 0 | 9H | — | 3C,5H | — | 7G | — |
| MORNING GLORY | — | 4C,9H | 2C,5G | 9C | — | 3C,7H | — | 3C,9G | — |
| COCKLEBUR | — | 4G | 2G | 4G | — | 2C,4G | — | 2C,8G | — |
| NUTSEDGE | — | 2C,9G | 2G | 9G | — | 0 | — | 2C,7G | — |
| CRABGRASS | — | 3C,7G | 2G | 7G | — | 2C,5G | — | 0 | — |
| BARNYARD GRASS | — | 4C,8H | 2C,5G | 5C,9G | — | 3C,8H | — | 3C,9H | — |
| WILD OATS | — | 5C,9G | 0 | 3C,9G | — | 2C,3G | — | 0 | — |
| WHEAT | — | 9G | 7G | 8G | — | 4G | — | 0 | — |
| CORN | — | 0 | 0 | 0 | — | 0 | — | 1H | — |
| SOYBEAN | — | 1H | 0 | 4H | — | 0 | — | 0 | — |

TABLE A-continued

| | | | | | | | |
|---|---|---|---|---|---|---|---|
| RICE | — | 5C,9G | 2C,8G | 5C,9G | 5C,9G | 3C,9G | — | 3C,6G |
| SORGHUM | — | 4C,9G | 2C,5G | 9C | 5C,9G | 4C,9G | — | 2C,9G |
| CHEATGRASS | — | 5C,9G | 8G | 4C,9G | 4C,9G | 8G | — | 6G |
| SUGAR BEETS | — | 3C,6G | 1H | 5C,9G | 5C,9G | 3C,7G | — | 4C,8G |
| VELVETLEAF | — | 3C,7H | 0 | 9C | 3C,7H | 2G | — | 2G |
| GIANT FOXTAIL | — | 4C,9G | 2C,6G | 9C | 5C,9G | 3C,8G | — | 3G |
| BARLEY | — | 4C,9G | 7G | 5C,9G | 4C,9G | 2C,8G | — | 0 |

PREEMERGENCE

| | | | | | | | |
|---|---|---|---|---|---|---|---|
| COTTON | — | — | — | — | — | — | — | — |
| MORNING GLORY | — | — | — | — | — | — | — | — |
| COCKLEBUR | — | — | — | — | — | — | — | — |
| NUTSEDGE | — | — | — | — | — | — | — | — |
| CRABGRASS | — | — | — | — | — | — | — | — |
| BARNYARD GRASS | — | — | — | — | — | — | — | — |
| WILD OATS | — | — | — | — | — | — | — | — |
| WHEAT | — | — | — | — | — | — | — | — |
| CORN | — | — | — | — | — | — | — | — |
| SOYBEAN | — | — | — | — | — | — | — | — |
| RICE | — | — | — | — | — | — | — | — |
| SORGHUM | — | — | — | — | — | — | — | — |
| CHEATGRASS | — | — | — | — | — | — | — | — |
| SUGAR BEETS | — | — | — | — | — | — | — | — |
| VELVETLEAF | — | — | — | — | — | — | — | — |
| GIANT FOXTAIL | — | — | — | — | — | — | — | — |
| BARLEY | — | — | — | — | — | — | — | — |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*), and giant foxtail (*Setaria faberii*). The third pot was planted with wheat (*Triticum aestivum*), barley (*Hordeum vulgare*), wild buckwheat (*Polygonum convolvulus*), cheatgrass (*Bromus secalinus*), sugarbeet (*Beta vulgaris*), wild oat (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice, and teaweed. The second pan was planted with green foxtail, cocklebur, morningglory, cotton, johnsongrass, barnyardgrass, corn, soybean, and giant foxtail. The third pot was planted with wheat, barley, wild buckwheat, cheatgrass, sugarbeet, wild oat, viola, blackgrass, and rape. The three pans were sprayed preemergence with the chemicals dissolved in a non-phytotoxic solvent.

Treated plants and controls were maintained in the greenhouse for approximately 24 days, then all treated plants were compared to controls and visually rated for plant response.

Response ratings are based on a scale of 0 to 100 where 0=no effect, and 100=complete control. A dash (—) response means no test.

Response ratings are contained in Table B.

TABLE B

| RATE RATE = G/HA | CMPD 1 | | | | | CMPD 3 | | | | | CMPD 5 | | | | CMPD 6 | | |
|---|---|---|---|---|---|---|---|---|---|---|---|---|---|---|---|---|---|
| | 0001 | 0004 | 0016 | 0062 | 0250 | 0001 | 0004 | 0016 | 0062 | 0250 | 0001 | 0004 | 0016 | 0062 | 0001 | 0004 | 0016 |
| POSTEMERGENCE | | | | | | | | | | | | | | | | | |
| GIANT FOXTAIL | 30 | 50 | 70 | 100 | — | 30 | 50 | 80 | — | — | — | 0 | 30 | 70 | 30 | 60 | 90 |
| VELVETLEAF | 30 | 60 | 90 | 100 | — | 30 | 50 | 70 | 90 | — | — | 30 | 50 | 90 | 30 | 50 | 70 |
| SUGAR BEETS | 50 | 70 | 100 | 100 | — | 80 | 100 | 100 | — | — | — | 0 | 0 | 100 | 70 | 90 | 100 |
| CRABGRASS | 0 | 30 | 50 | 80 | — | 30 | 50 | 70 | 90 | — | — | 0 | 0 | 0 | 0 | 0 | 30 |
| TEAWEED | 30 | 50 | 70 | 90 | — | 0 | 30 | 60 | 90 | — | — | 0 | 0 | 60 | 0 | 30 | 50 |
| JIMSONWEED | 30 | 50 | 70 | 100 | — | 50 | 70 | 90 | 100 | — | — | 30 | 60 | 90 | 30 | 50 | 70 |
| RICE | 40 | 70 | 100 | 100 | — | 50 | 100 | 100 | 100 | — | — | 0 | 30 | 60 | 0 | 0 | 70 |
| COCKLEBUR | 0 | 0 | 30 | 70 | — | 30 | 50 | 70 | 90 | — | — | 0 | 30 | 50 | 0 | 30 | 60 |
| COTTON | 0 | 30 | 50 | 70 | — | 0 | 30 | 50 | 70 | — | — | 0 | 0 | 60 | 0 | 0 | 30 |
| SOYBEAN | 0 | 0 | 60 | 80 | — | 30 | 50 | 80 | — | — | — | 0 | 0 | 70 | 0 | 0 | 70 |
| BARNYARD GRASS | 30 | 60 | 100 | 100 | — | 40 | 60 | 100 | 100 | — | — | 0 | 30 | 70 | 30 | 60 | 90 |
| WILD OATS | 0 | 0 | 30 | 70 | — | 30 | 50 | 70 | — | — | — | 0 | 0 | 0 | 0 | 0 | 50 |
| MORNINGGLORY | 30 | 60 | 90 | 100 | — | 30 | 50 | 70 | 90 | — | — | 0 | 40 | 70 | 50 | 70 | 80 |
| WHEAT | 0 | 20 | 30 | 60 | — | 30 | 50 | 70 | — | — | — | 0 | 0 | 0 | 0 | 30 | 60 |
| CASSIA | 0 | 0 | 30 | 50 | — | 30 | 50 | 70 | 100 | — | — | 0 | 30 | 80 | 0 | 0 | 30 |
| JOHNSONGRASS | 30 | 60 | 100 | 100 | — | 50 | 90 | 100 | 100 | — | — | 0 | 30 | 70 | 30 | 50 | 70 |
| NUTSEDGE | 0 | 30 | 60 | 90 | — | 30 | 60 | 90 | 100 | — | — | 0 | 0 | 80 | 0 | 30 | 50 |
| CORN | 0 | 0 | 0 | 0 | — | 0 | 0 | 0 | — | — | — | 0 | 0 | 0 | 0 | 0 | 0 |
| WILD BUCKWHEAT | 0 | 30 | 50 | 80 | — | 30 | 50 | 70 | — | — | — | 0 | 30 | 50 | 0 | 0 | 30 |
| BLACK GRASS | 0 | 30 | 50 | 80 | — | 0 | 0 | 30 | — | — | — | 0 | 40 | 70 | 30 | 50 | 70 |
| RAPESEED | 70 | 100 | 100 | 100 | — | 90 | 100 | 100 | — | — | — | 0 | 70 | 100 | 100 | 100 | 100 |
| BARLEY | 0 | 30 | 60 | 100 | — | 30 | 60 | 80 | — | — | — | 0 | 0 | 0 | 0 | 0 | 50 |
| GREEN FOXTAIL | 30 | 50 | 70 | 100 | — | 30 | 50 | 70 | 90 | — | — | 0 | 30 | 70 | 30 | 50 | 70 |
| CHEAT GRASS | 0 | 30 | 60 | 100 | — | 30 | 50 | 70 | — | — | — | 0 | 30 | 60 | 0 | 30 | 60 |
| BUCKWHEAT | — | — | — | — | — | — | — | — | — | — | — | — | — | — | — | — | — |
| VIOLA | — | — | — | — | — | 0 | 0 | 100 | — | — | — | 0 | 30 | 70 | 50 | 70 | 100 |
| LAMBSQUARTER | 50 | 70 | 90 | 100 | — | 50 | 70 | 90 | 100 | — | — | 0 | 30 | 100 | 30 | 50 | 70 |
| PREEMERGENCE | | | | | | | | | | | | | | | | | |
| GIANT FOXTAIL | — | 30 | 50 | 90 | 100 | — | 0 | 30 | 60 | 100 | — | — | 30 | 90 | — | 0 | 30 |
| VELVETLEAF | — | 0 | 30 | 60 | 90 | — | 0 | 30 | 50 | 80 | — | — | 30 | 80 | — | 0 | 30 |
| SUGAR BEETS | — | 30 | 50 | 70 | 90 | — | 70 | 80 | 90 | 100 | — | — | 0 | 90 | — | 30 | 60 |
| CRABGRASS | — | 0 | 30 | 50 | 100 | — | 0 | 30 | 60 | 90 | — | — | 0 | 50 | — | 0 | 0 |
| TEAWEED | — | 0 | 30 | 50 | 80 | — | 0 | 30 | 50 | 80 | — | — | 0 | 80 | — | 0 | 30 |
| JIMSONWEED | — | 0 | 30 | 60 | 90 | — | 30 | 50 | 70 | 90 | — | — | 30 | 80 | — | 0 | 30 |
| RICE | — | 80 | 100 | 100 | 100 | — | 70 | 90 | 100 | 100 | — | — | 0 | 100 | — | 30 | 70 |
| COCKLEBUR | — | 0 | 30 | 70 | 100 | — | 0 | 30 | 60 | 100 | — | — | 30 | 100 | — | 0 | 30 |
| COTTON | — | 0 | 20 | 40 | 60 | — | 0 | 30 | 50 | 70 | — | — | 0 | 70 | — | 0 | 0 |
| SOYBEAN | — | 0 | 0 | 20 | 60 | — | 0 | 30 | 70 | 90 | — | — | 0 | 60 | — | 0 | 0 |
| BARNYARD GRASS | — | 30 | 50 | 80 | 100 | — | 0 | 50 | 80 | 100 | — | — | 0 | 90 | — | 0 | 50 |
| WILD OATS | — | 0 | 0 | 30 | 60 | — | 0 | 30 | 50 | 70 | — | — | 0 | 60 | — | 0 | 0 |
| MORNINGGLORY | — | 0 | 0 | 50 | 80 | — | 30 | 50 | 70 | 90 | — | — | 0 | 90 | — | 0 | 0 |
| WHEAT | — | 0 | 20 | 30 | 60 | — | 0 | 0 | 50 | 70 | — | — | 0 | 30 | — | 0 | 20 |
| CASSIA | — | 0 | 30 | 50 | 70 | — | 0 | 30 | 60 | 90 | — | — | 50 | 100 | — | 0 | 30 |
| JOHNSONGRASS | — | 30 | 60 | 90 | 100 | — | 50 | 70 | 90 | 100 | — | — | 0 | 90 | — | 0 | 50 |
| NUTSEDGE | — | 0 | 30 | 50 | 100 | — | 0 | 0 | 30 | 90 | — | — | 100 | 100 | — | 30 | 50 |
| CORN | — | 0 | 0 | 0 | 0 | — | 0 | 0 | 0 | 0 | — | — | 0 | 40 | — | 0 | 0 |
| WILD BUCKWHEAT | — | 30 | 50 | 70 | 90 | — | 30 | 50 | 70 | 90 | — | — | 30 | 70 | — | 30 | 50 |
| BLACK GRASS | — | 0 | 30 | 60 | 90 | — | 30 | 50 | 70 | 100 | — | — | 30 | 80 | — | 50 | 70 |
| RAPESEED | — | 50 | 70 | 90 | 100 | — | 70 | 80 | 90 | 100 | — | — | 70 | 90 | — | 40 | 60 |
| BARLEY | — | 0 | 0 | 30 | 70 | — | 0 | 0 | 50 | 90 | — | — | 0 | 30 | — | 0 | 30 |
| GREEN FOXTAIL | — | 30 | 50 | 90 | 100 | — | 50 | 80 | 100 | 100 | — | — | 30 | 90 | — | 30 | 50 |

TABLE B-continued

| | | | | | | | | | | | | | | | | | |
|---|---|---|---|---|---|---|---|---|---|---|---|---|---|---|---|---|---|
| CHEAT GRASS | — | 0 | 30 | 50 | 80 | — | 30 | 60 | 90 | 100 | — | — | 50 | 80 | — | 0 | 30 |
| BUCKWHEAT | — | — | — | — | — | — | — | — | — | — | — | — | — | — | — | — | — |
| VIOLA | — | — | — | — | — | — | 30 | 50 | 70 | 100 | — | — | 0 | 100 | — | 30 | 60 |
| LAMBSQUARTER | — | 30 | 60 | 100 | 100 | — | 30 | 60 | 90 | 100 | — | — | 70 | 90 | — | 50 | 70 |

| | CMPD 6 | | CMPD 10 | | | | CMPD 12 | | | | | |
|---|---|---|---|---|---|---|---|---|---|---|---|---|
| RATE RATE = G/HA | 0062 | 0250 | 0004 | 0016 | 0062 | 0250 | 0001 | 0004 | 0016 | 0062 | 0250 | 0.25 |
| POSTEMERGENCE | | | | | | | | | | | | |
| GIANT FOXTAIL | 100 | — | 0 | 50 | 60 | — | 20 | 70 | 90 | 95 | — | 10 |
| VELVETLEAF | 90 | — | 20 | 60 | 80 | — | — | 0 | 80 | — | — | 0 |
| SUGAR BEETS | — | — | 20 | 0 | 90 | — | 30 | 100 | 100 | 100 | — | 20 |
| CRABGRASS | 50 | — | 0 | 0 | 0 | — | — | 50 | 60 | 80 | — | 20 |
| TEAWEED | 70 | — | 0 | 40 | 50 | — | — | 20 | 50 | 70 | — | 20 |
| JIMSONWEED | 100 | — | 0 | 20 | 50 | — | — | 50 | 50 | 85 | — | 0 |
| RICE | 90 | — | 0 | 50 | 90 | — | — | 90 | 100 | 100 | — | 40 |
| COCKLEBUR | 90 | — | 0 | 50 | 70 | — | 0 | 0 | 30 | 100 | — | 0 |
| COTTON | 70 | — | 0 | 20 | 50 | — | 20 | 70 | 80 | 85 | — | 10 |
| SOYBEAN | — | — | 0 | 40 | 70 | — | 20 | 30 | 50 | 85 | — | 10 |
| BARNYARD GRASS | 100 | — | 20 | 70 | 100 | — | 60 | 100 | 100 | 100 | — | 50 |
| WILD OATS | — | — | 0 | 70 | 20 | — | 20 | 60 | 60 | 80 | — | 20 |
| MORNINGGLORY | 90 | — | 30 | 40 | 80 | — | 60 | 70 | 90 | 100 | — | 20 |
| WHEAT | — | — | 0 | 40 | 60 | — | 80 | 100 | 100 | 100 | — | 40 |
| CASSIA | 60 | — | 0 | 30 | 60 | — | — | 0 | — | 100 | — | 0 |
| JOHNSONGRASS | 90 | — | 20 | 80 | 100 | — | 60 | 100 | 100 | 100 | — | 50 |
| NUTSEDGE | 70 | — | 0 | 0 | 40 | — | — | 70 | 70 | 100 | — | 0 |
| CORN | — | — | 0 | 30 | 50 | — | 0 | 0 | 0 | 10 | — | 0 |
| WILD BUCKWHEAT | — | — | 0 | 20 | 80 | — | 0 | 0 | 70 | 90 | — | 0 |
| BLACK GRASS | — | — | 0 | 50 | 80 | — | 40 | 70 | 80 | 100 | — | 30 |
| RAPESEED | — | — | 0 | 100 | 100 | — | 70 | 100 | 100 | 100 | — | 70 |
| BARLEY | — | — | 0 | 30 | 70 | — | 60 | 90 | 100 | 100 | — | 20 |
| GREEN FOXTAIL | 100 | — | 0 | 30 | 60 | — | 30 | 70 | 90 | 95 | — | 20 |
| CHEAT GRASS | — | — | 0 | 20 | 40 | — | 50 | 80 | 70 | 100 | — | 20 |
| BUCKWHEAT | — | — | — | — | — | — | — | — | — | — | — | — |
| VIOLA | — | — | 0 | 30 | 50 | — | 20 | 20 | 50 | 90 | — | 20 |
| LAMBSQUARTER | 100 | — | 30 | 70 | 80 | — | — | 50 | 80 | 95 | — | 0 |
| PREEMERGENCE | | | | | | | | | | | | |
| GIANT FOXTAIL | 70 | 90 | — | 40 | 70 | 80 | 0 | 20 | 80 | 100 | 100 | — |
| VELVETLEAF | 70 | 90 | — | 20 | 50 | 90 | 0 | 0 | 10 | 85 | 80 | — |
| SUGAR BEETS | 80 | 90 | — | 30 | 70 | 80 | 0 | 30 | 80 | 95 | 95 | — |
| CRABGRASS | 30 | 60 | — | 0 | 0 | 20 | 0 | 20 | 30 | 85 | 90 | — |
| TEAWEED | 50 | 80 | — | 0 | 60 | 90 | 0 | 20 | 0 | 80 | 95 | — |
| JIMSONWEED | 60 | 90 | — | 0 | 30 | 70 | 0 | 20 | 0 | 80 | 100 | — |
| RICE | 100 | 100 | — | 50 | 90 | 100 | 10 | 60 | 80 | — | — | — |
| COCKLEBUR | 50 | 90 | — | 0 | — | 50 | 0 | 20 | 20 | 70 | 80 | — |
| COTTON | 30 | 60 | — | 0 | 20 | 50 | 0 | 0 | 20 | 80 | 85 | — |
| SOYBEAN | 20 | 70 | — | 0 | 0 | 20 | 0 | 10 | 20 | 30 | 90 | — |
| BARNYARD GRASS | 70 | 90 | — | 30 | 80 | 90 | 10 | 20 | 70 | 100 | 100 | — |
| WILD OATS | 30 | 60 | — | 0 | 0 | 20 | 20 | 30 | 50 | 60 | 70 | — |
| MORNINGGLORY | 50 | 70 | — | 0 | 30 | 40 | 0 | 0 | 20 | 80 | 85 | — |
| WHEAT | 40 | 80 | — | 0 | 0 | 20 | 0 | 20 | 30 | 90 | 100 | — |
| CASSIA | 60 | 90 | — | 0 | 20 | 70 | — | — | — | — | — | — |
| JOHNSONGRASS | 80 | 90 | — | 60 | 100 | 100 | 65 | 60 | 100 | 100 | 100 | — |
| NUTSEDGE | 80 | 100 | — | 0 | 0 | 30 | 0 | 0 | 80 | 90 | 100 | — |
| CORN | 0 | 0 | — | 20 | 0 | 0 | 0 | 0 | 10 | 20 | 20 | — |
| WILD BUCKWHEAT | 80 | 90 | — | 50 | 70 | 100 | 0 | 0 | 70 | 80 | 85 | — |
| BLACK GRASS | 90 | 100 | — | 50 | 80 | 90 | 50 | 70 | 80 | — | 95 | — |
| RAPESEED | 80 | 100 | — | 40 | 40 | 90 | 20 | 30 | 80 | 95 | 95 | — |
| BARLEY | 50 | 90 | — | 0 | 20 | 20 | 0 | 20 | 40 | 85 | 90 | — |
| GREEN FOXTAIL | 100 | 100 | — | 20 | 60 | 90 | 30 | 80 | 90 | 100 | 100 | — |
| CHEAT GRASS | 70 | 90 | — | 30 | 60 | 90 | 20 | 40 | 60 | 85 | 85 | — |
| BUCKWHEAT | — | — | — | — | — | — | — | — | — | — | — | — |
| VIOLA | 80 | 100 | — | 70 | 60 | 90 | — | — | — | — | — | — |
| LAMBSQUARTER | 80 | 90 | — | 20 | 80 | 90 | 0 | 0 | 70 | — | 95 | — |

Test C

Corn and Sorghum Test
Postemergence

Six round containers (18 cm diameter) were filled with Sassafras sandy loam soil. One container was planted with corn and a second container with soybeans. Two containers were planted with the grass species sorghum (*Sorghum bicolor*), green foxtail (*Setaria viridis*), johnsongrass (*Sorghum halepense*), barnyardgrass (*Echinochloa crusgalli*), fall panicum (*Panicum dichotomiflorum*), crabgrass (*Digitaria sanguinalis*) and nutsedge (*Cyperus rotundus*). Two containers were planted with the broadleaf species cocklebur (*Xanthium pensylvanicum*), morningglory (*Ipomoea hederacea*), velvetleaf (*Abutilon theophrasti*), jimsonweed (*Datura stramonium*), ragweed (*Ambrosia artemisifolia*), lambsquarters (*Chenopodium album*), pigweed (*Amaranthus retroflexus*), and smartweed (*Polygonum pensylvanicum*). The plants were grown 10–21 days, dependent on the species and then sprayed postemergence with the chemicals dissolved in a non-phytotoxic solvent.

Preemergence

Six round containers (18 cm diameter) were filled with Tama silt loam soil. The same species described in the postemergence section were planted and sprayed with the chemicals dissolved in a nonphytotoxic solvent.

Evaluations

Treated plants and controls were maintained in the greenhouse for approximately 28 days. Treated plants were then compared with control plants and rated for plant response.

Response ratings are based on a scale of 0 to 100, where 0=no effect, and 100=complete control. A dash (—) response means no test. The results are in Table C.

TABLE C

| | | CMPD 3 | | | | | | CMPD 6 | | | | | | CMPD 12 | | | | |
|---|---|---|---|---|---|---|---|---|---|---|---|---|---|---|---|---|---|---|
| RATE RATE VM/HA | 0002 | 0004 | 0008 | 0016 | 0031 | 0062 | 0125 | 0002 | 0004 | 0008 | 0016 | 0031 | 0062 | 0125 | 0002 | 0004 | 0008 | 0016 | 0031 | 0062 | 0125 |

POSTEMERGENCE

| | 0002 | 0004 | 0008 | 0016 | 0031 | 0062 | 0125 | 0002 | 0004 | 0008 | 0016 | 0031 | 0062 | 0125 | 0002 | 0004 | 0008 | 0016 | 0031 | 0062 | 0125 |
|---|---|---|---|---|---|---|---|---|---|---|---|---|---|---|---|---|---|---|---|---|---|
| CORN | 0 | 0 | 0 | 0 | 0 | 0 | 20 | — | 0 | 0 | 0 | 0 | 0 | 0 | 0 | 0 | 0 | 0 | 0 | 0 | 0 |
| SOYBEAN | 80 | 95 | 100 | 100 | 100 | 100 | 100 | — | 0 | 40 | 80 | 100 | 100 | 100 | 40 | 70 | 25 | 50 | 75 | 95 | 100 |
| GREEN FXTL | 50 | 70 | 85 | 95 | 100 | 100 | 100 | — | 0 | 0 | 25 | 35 | 75 | 100 | 45 | 75 | 90 | 100 | 100 | 100 | 100 |
| GIANT FXTL | 45 | 70 | 85 | 100 | 100 | 100 | 100 | — | 0 | 30 | 50 | 85 | 100 | 100 | 35 | 70 | 100 | 100 | 100 | 100 | 100 |
| PANICUM | 70 | 85 | 95 | 100 | 100 | 100 | 95 | — | 0 | 20 | 40 | 60 | 90 | 95 | 85 | 0 | 30 | 50 | 75 | 100 | 100 |
| CRABGRASS | 0 | 0 | 0 | 30 | 50 | 75 | 100 | — | 90 | 0 | 0 | 0 | 35 | 40 | 0 | 0 | 30 | 50 | 100 | 100 | 100 |
| BARNYARDGRASS | 90 | 100 | 100 | 100 | 100 | 100 | 100 | — | 95 | 100 | 100 | 100 | 100 | 100 | 85 | 100 | 100 | 100 | 100 | 100 | 100 |
| JOHNSONGRASS | 100 | 100 | 100 | 100 | 100 | 100 | 100 | — | 90 | 100 | 100 | 100 | 100 | 100 | 90 | 100 | 100 | 100 | 100 | 100 | 100 |
| SORGHUM | 90 | 95 | 100 | 100 | 95 | 100 | 100 | — | 0 | 20 | 55 | 65 | 75 | 100 | 100 | 45 | 70 | 85 | 80 | 100 | 100 |
| NUTSEDGE | 35 | 70 | 85 | 95 | 85 | 90 | 100 | — | 0 | 0 | 25 | 50 | 70 | 85 | 20 | 35 | 45 | 65 | 65 | 60 | 85 |
| VELVETLEAF | 30 | 45 | 65 | 70 | 100 | 90 | 100 | — | 0 | 35 | 65 | 85 | 95 | 100 | 0 | 0 | 30 | 50 | 100 | 80 | 100 |
| COCKLEBUR | 80 | 90 | 100 | 100 | 100 | 100 | 100 | — | 0 | 60 | 70 | 85 | 100 | 80 | 50 | 0 | 90 | 95 | 100 | 100 | 100 |
| SMARTWEED | 35 | 50 | 80 | 95 | 100 | 100 | 100 | — | 40 | 0 | 25 | 40 | 65 | 80 | 0 | 50 | 25 | 55 | 75 | 90 | 95 |
| LAMBSQUARTER | 60 | 70 | 90 | 95 | 100 | 100 | 100 | — | 60 | 65 | 85 | 100 | 100 | 100 | 75 | 100 | 100 | 100 | 100 | 100 | 100 |
| PIGWEED | 90 | 100 | 100 | 100 | 100 | 100 | 100 | — | 0 | 30 | 60 | 40 | 80 | 80 | 60 | 85 | 95 | 100 | 95 | 100 | 100 |
| MORNINGGLORY | 70 | 85 | 95 | 100 | 100 | 100 | 100 | — | 35 | 50 | — | 75 | — | 90 | 35 | 65 | 85 | 95 | 100 | 100 | 100 |
| JIMSONWEED | 55 | 70 | 90 | 100 | 100 | 100 | 100 | — | — | — | — | — | — | — | — | — | — | — | — | — | — |
| RAGWEED | — | — | — | — | — | — | — | — | — | — | — | — | — | — | — | — | — | — | — | — | — |
| CORN ERLY INJ | — | — | — | — | — | — | — | — | — | — | — | — | — | — | — | — | — | — | — | — | — |

PREEMERGENCE

| | 0002 | 0004 | 0008 | 0016 | 0031 | 0062 | 0125 | 0002 | 0004 | 0008 | 0016 | 0031 | 0062 | 0125 | 0002 | 0004 | 0008 | 0016 | 0031 | 0062 | 0125 |
|---|---|---|---|---|---|---|---|---|---|---|---|---|---|---|---|---|---|---|---|---|---|
| CORN | — | — | — | — | 0 | 0 | 0 | — | — | — | — | 0 | 0 | 0 | 0 | 0 | — | 0 | 0 | 0 | 0 |
| SOYBEAN | — | — | — | 0 | 0 | 0 | 0 | — | — | — | — | 0 | 0 | 0 | 0 | 0 | — | 0 | 0 | 0 | 0 |
| GREEN FXTL | — | — | — | 0 | 20 | 40 | 65 | — | — | — | — | 0 | 20 | 55 | 40 | 75 | — | 0 | 20 | 60 | 90 |
| GIANT FXTL | — | — | — | 0 | 25 | 40 | 60 | — | — | — | — | 0 | 20 | 60 | 45 | 70 | — | 0 | 20 | 60 | 95 |
| PANICUM | — | — | — | 35 | 60 | 95 | 100 | — | — | — | — | 0 | 30 | 75 | 35 | 70 | — | 40 | 70 | 95 | 100 |
| CRABGRASS | — | — | — | 0 | 0 | 0 | 20 | — | — | — | — | 0 | 0 | 0 | 0 | 0 | — | 0 | 0 | 25 | 45 |
| BARNYARDGRASS | — | — | — | 0 | 0 | 30 | 65 | — | — | — | — | 0 | 25 | 40 | 50 | 100 | — | 0 | 0 | 40 | 75 |
| JOHNSONGRASS | — | — | — | 0 | 35 | 65 | 80 | — | — | — | — | 0 | 60 | 100 | 100 | 100 | — | 45 | 80 | 100 | 100 |
| SORGHUM | — | — | — | 0 | 20 | 65 | 100 | — | — | — | — | 0 | 50 | 80 | 95 | 100 | — | 30 | 70 | 95 | 85 |
| NUTSEDGE | — | — | — | 0 | 0 | 0 | 40 | — | — | — | — | 0 | 0 | 30 | 60 | 85 | — | 0 | 25 | 60 | 0 |
| VELVETLEAF | — | — | — | 0 | 0 | 0 | 0 | — | — | — | — | 0 | 0 | 35 | 0 | 0 | — | 0 | 0 | 0 | 0 |
| COCKLEBUR | — | — | — | 0 | 25 | 60 | 90 | — | — | — | — | 35 | 35 | 0 | 50 | 0 | — | 0 | 30 | 80 | 100 |
| SMARTWEED | — | — | — | 20 | 40 | 65 | 85 | — | — | — | — | 25 | 70 | 45 | 75 | 100 | — | 0 | 20 | 65 | 85 |
| LAMBSQUARTER | — | — | — | 20 | 35 | 65 | 90 | — | — | — | — | 25 | 45 | 55 | 60 | 85 | — | 0 | 35 | 80 | 100 |
| PIGWEED | — | — | — | 0 | 0 | 0 | 0 | — | — | — | — | 0 | 0 | 20 | 35 | 80 | — | 0 | 20 | 0 | 0 |
| MORNINGGLORY | — | — | — | 0 | 0 | 0 | 35 | — | — | — | — | 0 | 0 | 40 | 0 | 40 | — | 0 | 0 | 0 | 40 |
| JIMSONWEED | — | — | — | — | — | — | — | — | — | — | — | — | — | — | — | — | — | — | — | — | — |
| RAGWEED | — | — | — | — | — | — | — | — | — | — | — | — | — | — | — | — | — | — | — | — | — |
| CORN ERLY INJ | — | — | — | — | — | — | — | — | — | — | — | — | — | — | — | — | — | — | — | — | — |

Test D

Postmergence Grass Control in Corn

Johnsongrass (*Sorghum halepense*), shattercane (*Sorghum bicolor*), giant foxtail (*Setaria faberii*), quackgrass (*Agropyron repens*) and barnyardgrass (*Echinochloa crusgalli*) were planted in 5" standard pots filled with Tama soil. Corn was planted in 7" pots filled with the same soil. When the corn was 12 days old, the shattercane, giant foxtail and barnyardgrass 14 days old, the johnsongrass 26 days old and the quackgrass 34 days old, they were all treated postemergence with the experimental material dissolved in a proprietary solvent. Twenty-three days after treatment, visual evaluation of plant injury was made. The results are shown in Table D.

TABLE D

| Rate g/ha | .5 | 1 | 2 | 4 | 16 | 16 | 31 | 62 | 125 |
|---|---|---|---|---|---|---|---|---|---|
| POSTEMERGENCE | | | | | | | | | |
| Quackgrass | 50 | 80 | 90 | 100 | 100 | 100 | 100 | 10 | 100 |
| Giant Foxtail | 30 | 40 | 65 | 85 | 95 | 100 | 100 | 100 | 100 |
| Shattercane | 30 | 60 | 70 | 75 | 90 | 95 | 100 | 100 | 100 |
| Barnyardgrass | 30 | 50 | 60 | 85 | 100 | 100 | 100 | 100 | 100 |
| Johnsongrass | 40 | 50 | 50 | 80 | 95 | 100 | 100 | 100 | 100 |
| Corn | 0 | 0 | 0 | 0 | 0 | 0 | 0 | 0 | 20 |

I claim:

1. A compound of the formula:

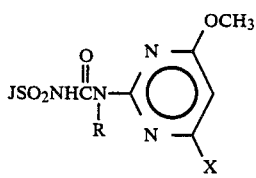

wherein

J is

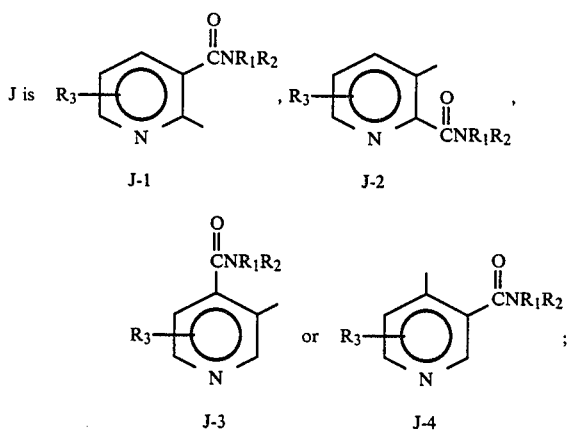

R is H or $CH_3$;
$R_1$ is H or $C_1$–$C_3$ alkyl;
$R_2$ is $C_1$–$C_3$ alkyl or $C_1$–$C_2$ alkoxy;
$R_3$ is H, Cl, F, Br, $CH_3$, $CF_3$, $OCH_3$ or $OCF_2H$; and
X is $CH_3$, $CH_2F$, $CH_2CH_3$, $OCH_3$, $OCH_2CH_3$, Cl, or $CH_2OCH_3$.

2. A compound of claim 1 where R is H.
3. A compound of claim 2 where J is J-1.
4. A compound of claim 2 where J is J-2.
5. A compound of claim 2 where J is J-3.
6. A compound of claim 2 where J is J-4.
7. A compound of claim 3 where X is $OCH_3$, $CH_3$ or Cl.
8. A compound of claim 7 where $R_3$ is H, F or Cl.
9. A compound of claim 8 where $R_2$ is $CH_3$, $CH_2CH_3$ or $OCH_3$; and $R_3$ is H.
10. A compound of claim 4 where X is $OCH_3$, $CH_3$ or Cl.
11. A compound of claim 10 where $R_3$ is H, F or Cl.
12. A compound of claim 11 where $R_2$ is $CH_3$, $CH_2CH_3$ or $OCH_3$; and $R_3$ is H.
13. A compound of claim 5 where X is $OCH_3$, $CH_3$ or Cl.
14. A compound of claim 13 where $R_3$ is H, F or Cl.
15. A compound of claim 14 where $R_2$ is $CH_3$, $CH_2CH_3$ or $OCH_3$; and $R_3$ is H.
16. A compound of claim 6 where X is $OCH_3$, $CH_3$ or Cl.
17. A compound of claim 16 where $R_3$ is H, F or Cl.
18. A compound of claim 17 where $R_2$ is $CH_3$, $CH_2CH_3$ or $OCH_3$; and $R_3$ is H.
19. The compound of claim 1 which is 2-[[(4,6-dimethoxypyrimidin-2-yl)aminocarbonyl]aminosulfonyl]-N,N-dimethyl-3-pyridinecarboxamide.
20. A composition suitable for controlling the growth of undesired vegetation which comprises an effective amount of a compound of claim 1 and at least one of the following: surfactant, solid or liquid diluent.
21. A composition suitable for controlling the growth of undesired vegetation which comprises an effective amount of a compound of claim 2 and at least one of the following: surfactant, solid or liquid diluent.
22. A composition suitable for controlling the growth of undesired vegetation which comprises an effective amount of a compound of claim 3 and at least one of the following: surfactant, solid or liquid diluent.
23. A composition suitable for controlling the growth of undesired vegetation which comprises an effective amount of a compound of claim 4 and at least one of the following: surfactant, solid or liquid diluent.
24. A composition suitable for controlling the growth of undesired vegetation which comprises an effective amount of a compound of claim 5 and at least one of the following: surfactant, solid or liquid diluent.
25. A composition suitable for controlling the growth of undesired vegetation which comprises an effective amount of a compound of claim 6 and at least one of the following: surfactant, solid or liquid diluent.
26. A composition suitable for controlling the growth of undesired vegetation which comprises an effective amount of a compound of claim 7 and at least one of the following: surfactant, solid or liquid diluent.
27. A composition suitable for controlling the growth of undesired vegetation which comprises an effective amount of the compound of claim 19 and at least one of the following: surfactant, solid or liquid diluent.
28. A method for controlling the growth of undesired vegetation which comprises applying to the locus to be protected an effective amount of a compound of claim 1.
29. A method for controlling the growth of undesired vegetation which comprises applying to the locus to be protected an effective amount of a compound of claim 2.
30. A method for controlling the growth of undesired vegetation which comprises applying to the locus to be protected an effective amount of a compound of claim 3.

31. A method for controlling the growth of undesired vegetation which comprises applying to the locus to be protected an effective amount of a compound of claim 4.

32. A method for controlling the growth of undesired vegetation which comprises applying to the locus to be protected an effective amount of a compound of claim 5.

33. A method for controlling the growth of undesired vegetation which comprises applying to the locus to be protected an effective amount of a compound of claim 6.

34. A method for controlling the growth of undesired vegetation which comprises applying to the locus to be protected an effective amount of a compound of claim 7.

35. A method for controlling the growth of undesired vegetation which comprises applying to the locus to be protected an effective amount of a compound of claim 8.

36. The method for controlling the growth of undesired vegetation in corn which comprises applying to the locus to be protected an effective amount of the compound of claim 19.

* * * * *